United States Patent [19]

Tsuneki et al.

[11] Patent Number: 5,543,546

[45] Date of Patent: Aug. 6, 1996

[54] PROCESS FOR PREPARING CARBONATE ESTERS

[75] Inventors: Hideaki Tsuneki, Tokyo; Yoshiyuki Onda, Suita; Atusi Moriya, Suita; Hiroshi Yoshida, Suita, all of Japan

[73] Assignee: Nippon Shokubai Co., Ltd., Osaka, Japan

[21] Appl. No.: 443,753

[22] Filed: May 18, 1995

[30] Foreign Application Priority Data

May 25, 1994 [JP] Japan .................................. 6-110972
May 31, 1994 [JP] Japan .................................. 6-119008
Jul. 5, 1994 [JP] Japan .................................. 6-153802

[51] Int. Cl.$^6$ .................................................... C07C 68/06
[52] U.S. Cl. .............................................. 558/270; 558/274
[58] Field of Search ................................ 558/274, 270

[56] References Cited

U.S. PATENT DOCUMENTS

| | | |
|---|---|---|
| 1,898,687 | 2/1933 | Rice . |
| 3,328,439 | 6/1967 | Hamilton ............................ 560/109 X |
| 4,045,464 | 8/1977 | Romano et al. .................... 260/463 |
| 4,182,726 | 1/1980 | Illuminati et al. ................. 260/463 |
| 4,533,504 | 8/1985 | Bolon et al. ....................... 260/463 |
| 5,210,268 | 5/1993 | Fukuoka et al. ................... 558/270 |
| 5,349,102 | 9/1994 | Tuinstra et al. ................... 558/270 X |

FOREIGN PATENT DOCUMENTS

| | | |
|---|---|---|
| 0623581 | 11/1994 | European Pat. Off. . |
| 48-036131A | 5/1973 | Japan . |
| 51-054525A | 5/1976 | Japan . |
| 54-048733A | 4/1979 | Japan . |
| 59-80636 | 5/1984 | Japan . |
| 62-8091B | 2/1987 | Japan . |
| 64-3181B | 1/1989 | Japan . |
| 4-122451 | 4/1992 | Japan . |
| 5-148189 | 6/1993 | Japan . |
| 6-298700A | 10/1994 | Japan . |
| WO92/09555 | 6/1992 | WIPO . |

OTHER PUBLICATIONS

Jean Barry et al., *Tetrahedron Letters*, vol. 29, No. 36, pp. 4567–4568, 1988, "Organic Syntheses Without Solvent: Base–Catalysed Ester Interchange".

*Primary Examiner*—Johann Richter
*Assistant Examiner*—Michael G. Ambrose
*Attorney, Agent, or Firm*—Ronald J. Kubovcik

[57] ABSTRACT

Carboxylate (1) of the formula $R^1COOR^2$ (where each of $R^1$ and $R^2$ independently represents an alkyl group, an alicyclic hydrocarbon group or an aryl alkyl group), an aromatic hydroxy compound of the formula $R^3OH$ (where $R^3$ represents an aromatic group with or without a substituent), and a catalyst are supplied to a batch reactor 1, and a transesterification between the carboxylate (1) and the aromatic hydroxy compound is performed to produce carboxylate (3) of the formula $R^1COOR^3$ (where $R^1$ and $R^3$ are as defined above). After distilling off the by-produced alcohol and unreacted compounds using a distillation column 2, carbonate ester (4) of the formula $R^4O$—$COOR^5$ (where each of $R^4$ and $R^5$ independently represents an alkyl group, an alicyclic hydrocarbon group or an aryl alkyl group) is supplied to the batch reactor 1. Then, a transesterification between the carboxylate (3) and the carbonate ester (4) is performed to produce carbonate ester (5) of the formula $R^3O$—$COOR^6$ (where $R^3$ is as defined above, and $R^6$ is a substituent selected from the group consisting of $R^3$, $R^4$ and $R^5$). This process enables efficient preparation of carbonate esters.

31 Claims, 10 Drawing Sheets

PROCESS FOR PREPARING CARBONATE ESTERS

FIELD OF THE INVENTION

The present invention relates to a process for preparing carbonate esters using raw carbonate esters and aromatic hydroxy compounds as raw materials.

The produced carbonate esters are industrially useful compounds and, for example, a diphenyl carbonate as one type of carbonate esters is used as a raw material for polycarbonates.

BACKGROUND OF THE INVENTION

A known conventional process for preparing aromatic carbonate esters carries out a transesterification between an aliphatic carbonate ester and an aromatic hydroxy compound or aromatic carboxylate wherein an alkoxyl group is an aromatic group. In particular, with respect to a process for preparing diphenyl carbonate by reacting a dimethyl carbonate as one type of aliphatic carbonate esters with phenol as one type of aromatic hydroxy compounds by way of methylphenyl carbonate, various proposals have been made. For example, the following four publications disclose known processes for preparing diphenyl carbonate. U.S. Pat. No. 4,045,464 uses Lewis acid or a compound producing Lewis acid as a catalyst. U.S. Pat. No. 4,182,726 uses a titanium compound or an aluminum compound as a catalyst. Japanese Publication for Examined Patent Application No. 3181/1989 (Tokukosho 64-3181) uses a lead compound as a catalyst. Japanese Publication for Unexamined Patent Application No. 48733/1979 (Tokukaisho 54-48733) uses an organotin compound as a catalyst.

All of the above-mentioned processes are carried out using a batch system, and methanol as a by-product is distilled off while supplying dimethyl carbonate to a reaction system. Thus, this process suffers from drawbacks including a long reaction time and low productivity. Moreover, in order to efficiently distill off methanol, a known process (Japanese Publication for Examined Patent Application No. 8091/1987 (Tokukosho 62-8091)) adds benzene to the reaction system. However, this process requires a complicated collection operation, for example, extracting methanol from a mixed solution of benzene and the methanol using water, when collecting the methanol. Thus, this process also failed to achieve sufficiently high productivity.

U.S. Pat. No. 5,210,268 discloses a process for preparing methylphenyl carbonate by reacting dimethyl carbonate and phenol in a continuous multistage distillation column. In this process, however, the conversion of dimethyl carbonate is about 1.6 mole percent to 24 mole percent, resulting in low productivity. Additionally, in this process, an object, diphenyl carbonate, is obtained by a disproportionation of methylphenyl carbonate, and therefore an increased number of processes is required to obtain the diphenyl carbonate compared with the above-mentioned processes.

The reason why the conversion of dimethyl carbonate is low is as follows. A transesterification reaction for producing methylphenyl carbonate is an equilibrium reaction (equilibrium constant $K=10^{-3}$ to $10^{-4}$) in which the equilibrium is extremely biased toward the original system and the reaction substantially does not progress.

U.S. Pat. No. 4,533,504 discloses a process for preparing diphenyl carbonate by reacting dimethyl carbonate and phenyl acetate. This process achieves high conversion of dimethyl carbonate, not lower than 70 mole percent. However, in this process, a batch system is used, and it is necessary to convert methyl acetate to diketene at very high temperatures and react the diketene with phenol when reproducing phenyl acetate from the by-produced methyl acetate. Consequently, the step of reproducing phenyl acetate gives a low yield, and the cost of service needs to be covered.

As described above, the conventional processes suffer from drawbacks including a low conversion and inefficient syntheses of raw materials. In the conventional process for preparing diphenyl carbonate by reacting dimethyl carbonate with phenol, since the dimethyl carbonate and the by-produced methanol form an azeotrope, it is difficult to separate them. In short, with this conventional process, it is impossible to efficiently prepare carbonate esters.

Then, there is a demand for a process capable of industrially preparing carbonate esters in an efficient manner.

With respect to industrial processes for preparing aromatic carboxylates, for example, the following processes are known. A process for esterifying aliphatic carboxylates with aromatic hydroxy compounds (Japanese Publication for Unexamined Patent Application No. 36131/1973 (Tokukaisho 48-36131) and No. 54525/1976 (Tokukaisho 51-54525)). A process for reacting isopropenyl acetate and phenol (Tetrahedron Letters, Vol. 29, No. 36, p.4567–4568, 1988). A process of esterification with highly reactive raw materials such as diketene (U.S. Pat. No. 4,533,504).

However, with these conventional processes, aromatic carboxylates can not be efficiently prepared because the conversion is relatively low or the syntheses of raw materials is difficult. A process for industrially preparing aromatic carboxylates by a transesterification reaction between a suitable aliphatic carboxylate and aromatic hydroxy compound has not been known. The reason for this is that the transesterification reaction is an equilibrium reaction (equilibrium constant $K=10^{-3}$ to $10^{-4}$) in which the equilibrium is extremely biased toward the original system, the equilibrium conversion is not higher than several mole percent, and the reaction substantially does not progress.

SUMMARY OF THE INVENTION

An object of the present invention is to provide a novel process for efficiently preparing carbonate esters using a raw carbonate ester and an aromatic hydroxy compound as raw materials.

In order to achieve the object, a process for preparing carbonate esters according to present invention includes the steps of:

producing a carboxylate represented by formula (3)

$$R^1COOR^3 \tag{3},$$

wherein $R^1$ represents an alkyl group, an alicyclic hydrocarbon group or an aryl alkyl group, and $R^3$ represents an aromatic group with or without a substituent, by performing a transesterification between a raw carboxylate, as a raw material, of formula (1)

$$R^1COOR^2 \tag{1},$$

wherein each of $R^1$ and $R^2$ independently represents an alkyl group, an alicyclic hydrocarbon group or an aryl alkyl group, and an aromatic hydroxy compound of formula (2)

$$R^3OH \tag{2},$$

wherein $R^3$ represents an aromatic group with or without a substituent, in the presence of a catalyst; and producing a carbonate ester of formula (5)

$$R^3O-COOR^6 \qquad (5),$$

wherein $R^3$ represents an aromatic group with or without a substituent, and $R^6$ represents a substituent selected from the group consisting of $R^3$, an alkyl group, an alicyclic hydrocarbon group and an aryl alkyl group, by performing a transesterification between said produced carboxylate and a raw carbonate ester, as a raw material, of formula (4)

$$R^4O-COOR^5 \qquad (4),$$

wherein each of $R^4$ and $R^5$ independently represents an alkyl group, an alicyclic hydrocarbon group or an aryl alkyl group, in the presence of a catalyst.

This process enables efficient preparation of carbonate esters. Moreover, since this process does not use, as a raw material, phosgene which is employed by a conventional process, it is safer. Furthermore, this process does not use raw materials containing chlorine. It is therefore possible to obtain polycarbonates with improved quality by using the produced carbonate ester as a raw material.

For a fuller understanding of the nature and advantages of the invention, reference should be made to the ensuing detailed description taken in conjunction with the accompanying drawings.

BRIEF DESCRIPTION OF THE DRAWINGS

FIG. 1 is a block diagram showing a schematic structure of a reaction device preferably used in a process for preparing carbonate esters according to one embodiment of the present invention.

FIG. 2 is a block diagram showing a schematic structure of another reaction device preferably used in a process for preparing carbonate esters according to one embodiment of the present invention.

FIG. 3 is a block diagram showing a schematic structure of still another reaction device preferably used in a process for preparing carbonate esters according to one embodiment of the present invention.

FIG. 4 is a block diagram showing a schematic structure of yet another reaction device preferably used in a process for preparing carbonate esters according to one embodiment of the present invention.

FIG. 5 is a block diagram showing a schematic structure of a reaction device preferably used in a process for preparing carbonate esters and carboxylates according to one embodiment of the present invention.

FIG. 6 is a block diagram showing a schematic structure of another reaction device preferably used in a process for preparing carbonate esters and carboxylates according to one embodiment of the present invention.

FIG. 7 is a block diagram showing a schematic structure of a reaction device preferably used in a process for preparing carboxylates according to one embodiment of the present invention.

FIG. 8 is a block diagram showing a schematic structure of another reaction device preferably used in a process for preparing carbonate esters according to one embodiment of the present invention.

FIG. 9 is a block diagram showing a schematic structure of still another reaction device preferably used in a process for preparing carbonate esters according to one embodiment of the present invention.

FIG. 10 is a block diagram showing a schematic structure of yet another reaction device preferably used in a process for preparing carbonate esters according to one embodiment of the present invention.

DESCRIPTION OF THE PREFERRED EMBODIMENTS

Figure 1:
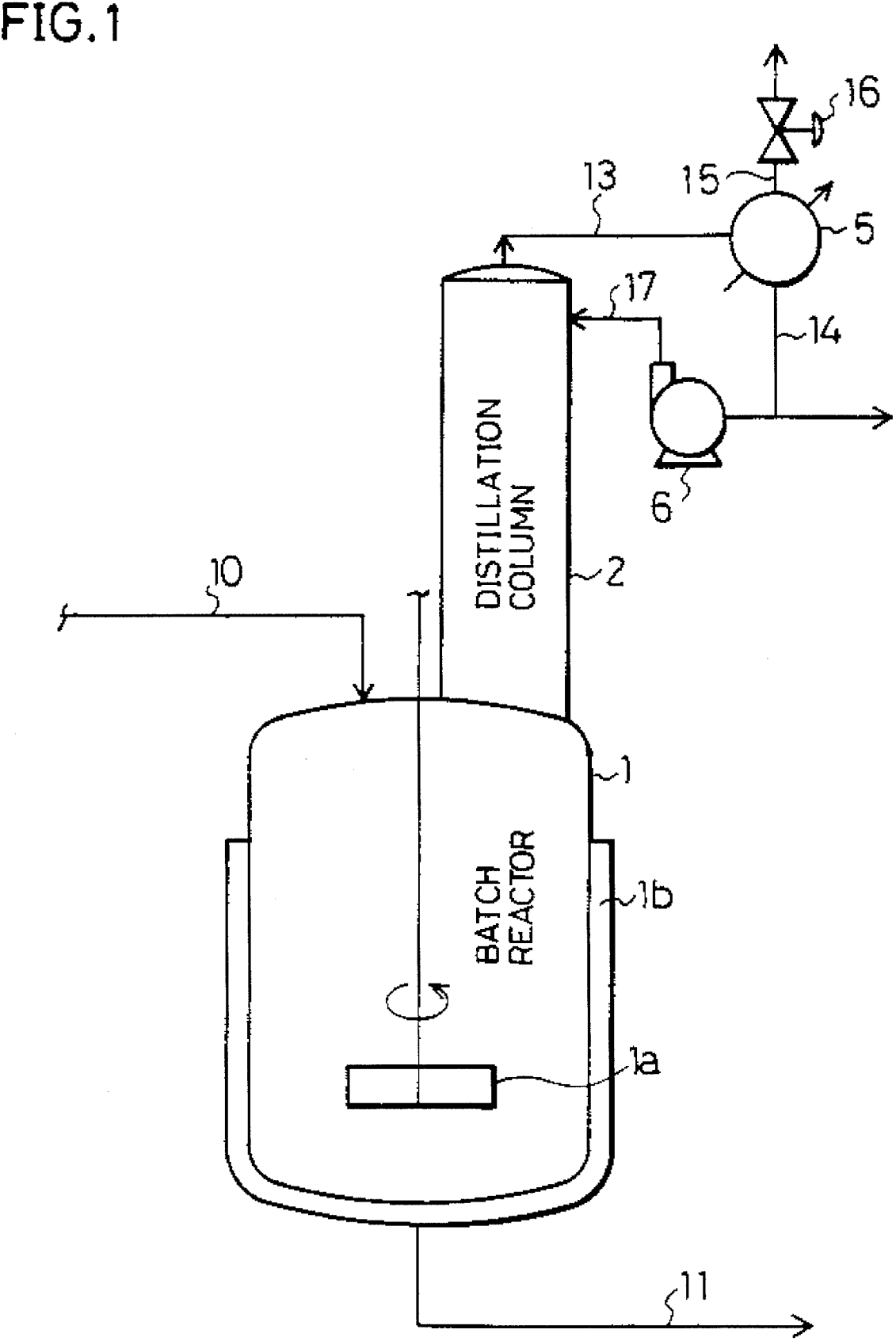
FIGS. 1 to 10 show one embodiment of the present invention.

The present invention will be described in detail below.

For the sake of explanation, a reaction for forming carboxylates represented by above-mentioned formula (3) is called a first-step reaction, and a reaction for forming carbonate esters represented by above-mentioned formula (5) is called a second-step reaction. Carboxylates represented by formula (3) and carbonate esters represented by formula (5) are hereinafter referred to as the carboxylates (3) and the carbonate esters (5), respectively. Among the carbonate esters (5), a carbonate ester (5) wherein a substituent represented by $R^6$ is a substituent $R^4$ or a substituent $R^5$ is referred to as carbonate monoester, and a carbonate ester (5) wherein a substituent represented by $R^6$ is a substituent $R^3$ is referred to as carbonate diester.

The second-step reaction is carried out in two stages, i.e., a reaction for forming carbonate monoester and a reaction for forming carbonate diester. Specifically, first, a transesterification between one of the substituents $R^4$ and $R^5$ of raw carbonate ester represented by above-mentioned formula (4) and the substituent $R^3$ of carboxylate (3) is carried out. Raw carbonate esters represented by formula (4) are hereinafter referred to as carbonate esters (4). As a result, carbonate monoester is produced, and carbonate ester is by-produced. Then, a transesterification between the residual substituent $R^4$ ($R^5$) of the carbonate monoester and the substituent $R^3$ of the carboxylate (3) is performed. As a result, carbonate diester is produced, and carboxylate is by-produced.

In a process for preparing carbonate esters according to the present invention, the type of a carboxylate represented by above-mentioned formula (1) is not limited as long as it is a compound wherein substituents represented by $R^1$ and $R^2$ in formula (1) are independently selected from the group consisting of an alkyl, an alicyclic hydrocarbon, and an aryl alkyl group. It is desirable to use an alkyl group of 1 to 10 carbons, an alicyclic hydrocarbon group of 3 to 10 carbons, and an aryl alkyl group of 7 to 10 carbons. Carboxylates represented by formula (1) are hereinafter referred to as carboxylates (1).

More specifically, examples of the carboxylate (1) are methyl acetate, ethyl acetate, propyl acetate, butyl acetate, cyclohexyl acetate, benzyl acetate, 2-ethylhexyl acetate, methyl propionate, ethyl propionate, propyl propionate, butyl propionate, methyl butyrate, ethyl butyrate, propyl butyrate, methyl isobutyrate, ethyl isobutyrate, propyl isobutyrate, methyl valerate, ethyl valerate, propyl valerate, methyl isovalerate, ethyl isovalerate, propyl isovalerate, methyl hexanoate, ethyl hexanoate, propyl hexanoate, methyl heptanoate, and ethyl heptanoate.

Carboxylate represented by formula (6)

$$R^1COOR^7 \qquad (6)$$

where $R^1$ represents an alkyl group, alicyclic hydrocarbon group, or aryl alkyl group, and $R^7$ represents a substituent selected from the group consisting of $R^4$ and $R^5$ is formed as a by-product at the time the carbonate ester (5) is produced. The carboxylate represented by formula (6) is hereinafter referred to as the carboxylate (6). The carboxylate (6) is preferably reusable as the carboxylate (1). It is therefore desirable to arrange the substituent $R^2$ of the carboxylate (1) and the substituents $R^4$ and $R^5$ of the carbonate ester (4) to be equal to each other. It is also desirable to select the substituents $R^2$, $R^4$ and $R^5$ so that the carboxylate (6) and the by-produced alcohol do not form an azeotrope. By satisfying these conditions, the separation and collection of the carboxylate (6) are easily performed. When the carboxylate (6) is entirely reusable as the carboxylate (1), the carboxylate (1) is not substantially consumed.

In the process for preparing carbonate esters according to the present invention, in order to improve the reaction efficiency (the equilibrium conversion) by biasing the equilibrium of the transesterification reaction toward the product system, it is desirable to remove from the reaction system an alcohol which is formed as a by-product by the first-step reaction and represented by formula (7)

$$R^2OH \tag{7}$$

wherein $R^2$ represents an alkyl group, an alicyclic hydrocarbon group, or an aryl alkyl group. Therefore, among the above-mentioned compounds, carboxylate (1) whose boiling point is higher than the boiling point of the by-produced alcohol is more preferred.

In order to further improve the reaction efficiency of the first-step reaction, it is desirable to use carboxylate (1) which does not form an azeotrope with the by-produced alcohol. Examples of such a carboxylate (1) are compounds including an acyl group having more than 3 carbons, such as ethyl butyrate, butyl butyrate, isovaleric acid ester, valerate and hexanoate, or compounds in which the substituent $R^1$ has more than 2 carbons. When carboxylate (1) satisfying the condition is used, it is logically possible to substantially completely convert carboxylate (1) to carboxylate (3).

In the process for preparing carbonate esters according to the present invention, the type of an aromatic hydroxy compound represented by above-mentioned formula (2) is not limited as long as the substituent represented by $R^3$ is an aromatic group. The aromatic group may have a substituent.

More specifically, the aromatic hydroxy compound represented by formula (2) is, for example, phenol, o-cresol, m-cresol, p-cresol, o-chlorophenol, m-chlorophenol, p-chlorophenol, o-ethylphenol, m-ethylphenol, p-ethylphenol, o-isopropylphenol, m-isopropylphenol, p-isopropylphenol, o-methoxyphenol, m-methoxyphenol, p-methoxyphenol, xylenols, α-naphthol, or β-naphthol. These aromatic hydroxy compounds may be suitably mixed for use. Among the listed compounds, phenol is suitable for industrial use.

In order to improve the equilibrium conversion of the aromatic hydroxy compound, it is desirable to use carboxylate (1) whose boiling point is lower than that of carboxylate (3) to be produced. With respect to combinations of such a carboxylate (1) and aromatic hydroxy compound, any combinations achieve improved equilibrium conversion except a combination of 2-ethylhexyl acetate and phenol and a combination of benzyl acetate and phenol. When the carboxylate (1) is acetate forming an alcohol of less than 8 carbons as a by-product or propionate forming an alcohol of less than 9 carbons as a by-product, it is possible to use the carboxylate (1) along with any of the above-mentioned aromatic hydroxy compounds. The carboxylate (1) and the carboxylate (3) are allowed to form an azeotrope.

More specifically, examples of the carboxylate (3) obtained by the above-mentioned first-step reaction are phenyl acetate, isomers of methylphenylacetate, isomers of ethylphenylacetate, isomers of chlorophenyl acetate, isomers of isopropylphenyl acetate, isomers of methoxyphenyl acetate, isomers of dimethylphenyl acetate, isomers of naphthyl acetate, isomers of methylphenyl propionate, phenyl butyrate, phenyl isobutyrate, phenyl valerate, isomers of methylphenyl valerate, phenyl isovalerate, phenyl hexanoate, and phenyl heptanoate.

In the process for preparing carbonate esters according to the present invention, the type of the carbonate ester (4) to be used as a raw material and represented by formula (4) is not particularly limited, but each of the substituents $R^4$ and $R^5$ in formula (4) is independently represents an alkyl, an alicyclic hydrocarbon, and an aryl alkyl group.. It is desirable to use an alkyl group of 1 to 10 carbons, an alicyclic hydrocarbon group of 3 to 10 carbons, and an aryl alkyl group of 7 to 10 carbons.

More specifically, the carbonate ester (4) is, for example, dimethyl carbonate, diethyl carbonate, di-n-propyl carbonate, diisopropyl carbonate, isomers of dibutyl carbonate, isomers of dipentyl carbonate, isomers of dihexyl carbonate, isomers of diheptyl carbonate, isomers of dioctyl carbonate, isomers of dinonyl carbonate, isomers of didecyl carbonate, dicyclohexyl carbonate, dibenzyl carbonate, isomers of diphenethyl carbonate, or isomers of di(methylbenzyl) carbonate. These carbonate esters (4) may be suitably mixed for use. Among the listed compounds, dimethyl carbonate is suitable for industrial use.

In the process for preparing carbonate esters according to the present invention, in order to improve the reaction efficiency (the equilibrium conversion) by biasing the equilibrium of the transesterification reaction toward the product system, it is desirable to continuously extract carboxylate (6) from the reaction system in the second-step reaction. Therefore, among the above-mentioned compounds, carboxylate (3) whose boiling point is higher than the boiling point of the by-produced carboxylate (6) is preferred. An example of a combination of the carboxylate (3) and the carbonate ester (4) is a carboxylate (3) wherein the substituent $R^3$ is a phenyl group and a carbonate ester (4) having less than 8 carbons when the substituents $R^4$ and $R^5$ form a straight chain.

Moreover, in order to continuously remove the produced carbonate ester (5) from the reaction system, it is desirable to use carboxylate (3) whose boiling point is lower than the boiling point of the carbonate ester (5). For example, the carboxylate (3) is a compound having less than 8 carbons when the substituent $R^1$ forms a straight chain.

Additionally, in order to achieve easy separation of the produced carbonate ester (5) and the carboxylate (3), a relatively large difference in the boiling point between the carboxylate (3) and the carbonate ester (5) is preferred. Meanwhile, in order to improve the equilibrium conversion of the carbonate ester (4), it is desired that the difference in the boiling point between the carboxylate (3) and the carbonate ester (4) is relatively small and the difference in the boiling point between the carboxylate (3) and the carboxylate (6) is relatively large.

The type of a reactor used for carrying out the first-step reaction and/or second-step reaction is not particularly limited. Thus, any of batch reactors, flow reactors, vapor-liquid contacting reactors is used. The flow reactor may be of a fluidized-bed type, a fixed-bed type (a simple piston-flow type when a homogeneous catalyst, to be described later, is used) or of a stirred-tank type. The first-step reaction and second-step reaction may be carried out by using the same reactor, or different reactors.

The first-step reaction is an equilibrium reaction (equilibrium constant $K=10^{-3}$ to $10^{-4}$) in which the equilibrium is extremely biased toward the original system. Therefore, in order to improve the reaction efficiency (equilibrium conversion) by biasing the equilibrium of the transesterification reaction toward the product system, it is desirable to extract from the reaction system an alcohol produced as a by-product at the time the carboxylate (3) is produced.

Therefore, when carrying out the first-step reaction using a batch reactor, and when carrying out the first-step reaction using a flow reactor, for example, a continuous tank reactor, it is desirable to use a method in which a distillation column is installed in an upper portion of the reactor and the by-produced alcohol is continuously removed (distilled) from the reaction system. When distillating off the alcohol, it is desirable to sufficiently separate the alcohol from the carboxylate (1).

The following is an efficient and preferred method for carrying out the first-step reaction using a vapor-liquid contacting reactor. In this method, the carboxylate (1) and an aromatic hydroxy compound are continuously supplied to the reactor, and a high boiling point component containing the produced carboxylate (3) is continuously removed in a liquid form from a lower portion of the reactor, while a low boiling point component containing the by-produced alcohol is continuously removed in a gaseous form from the upper portion of the reactor.

The second-step reaction is also an equilibrium reaction (equilibrium constant $K=10^{-1}$ to $10^1$), but the equilibrium of the transesterification reaction is not as much as biased toward the original system compared with the first-step reaction. Therefore, the second-step reaction is carried out more easily compared with the first-step reaction. However, similar to the above-mentioned first-step reaction, in order to improve the reaction efficiency (equilibrium conversion) by biasing the equilibrium of the transesterification reaction, it is desirable to remove from the reaction system the carboxylate (6) which is formed as a by-product at the time the carboxylate (5) is produced.

Thus, when carrying out the second-step reaction using a batch reactor, and when carrying out the second-step reaction using a flow reactor such as a continuous tank reactor, it is desirable to use a method in which a distillation column is installed in an upper portion of the reactor and the by-produced carboxylate (6) is continuously removed (distilled) from the reaction system. When distillating off the carboxylate (6), it is desirable to sufficiently separate the carboxylate (6) from the carboxylate (3).

The following is an efficient and preferred method for carrying out the second-step reaction using a vapor-liquid contacting reactor. In this method, carboxylate (3) and carbon ester (4) are continuously supplied to the reactor, and a high boiling point component containing the produced carboxylate (5) is continuously removed in a liquid form from a lower portion of the reactor, while a low boiling point component containing the by-produced carboxylate (6) is continuously removed in a gaseous form from an upper portion of the reactor.

The type of the vapor-liquid contacting reactor is not particularly limited, but it needs to have a structure in which a vapor-phase portion exists in the reactor and the produced low boiling point component is continuously separated and removed to the vapor-phase portion. In short, the vapor-liquid contacting reactor needs to have a structure capable of carrying out so-called reaction distillation. It is particularly desired to use a continuous multistage distillation column or a type of bubble column which supplies a raw material with a higher boiling point from an upper portion of the reactor and a raw material with a lower boiling point from a lower portion of the reactor.

As for the continuous multistage distillation column, a distillation column having more than one stage in addition to the top (topmost stage) and the bottom (bottommost stage) is preferred. Any columns which are generally used as distillation columns are employed as the multistage distillation columns. Examples of the generally-used distillation columns are packed columns packed with various packings, such as a Raschig ring, a Pall ring, an Intelox saddle, a Dixon packing, a McMahon packing and a Sulzer packing, and plate columns using trays (plates), such as a bubble cap tray, sieve tray and a valve tray. It is also possible to use a complex distillation column having both plates and a packing bed. It is also possible to use a combination of multistage distillation columns. The number of stages means the number of plates in a plate column and the theoretical number of stages in a packed column.

With respect to the bubble column, in order to efficiently perform vapor-liquid contacting, it is desired to use a bubble column having a distributor such as a perforated plate and a porous plate in a gas inlet section in a lower portion of the reactor. The bubble column may be gradually filled with packings. The bubble column may also be provided with a gas redistributor and a stage for preventing back mixing of liquid. Additionally, it is possible to improve the efficiency of vapor-liquid separation by installing a distillation column in an upper portion of the bubble column.

Moreover, a plurality of the above-mentioned multistage distillation columns and bubble columns may be joined so as to further improve the reaction efficiency. Furthermore, it is possible to use a combination of the above-mentioned batch reactor, flow reactor and vapor-liquid contacting reactor for the first-step reaction and/or the second-step reaction.

In the second-step reaction, when the boiling point of the carbonate ester (4) is lower than that of the carboxylate (6), if the carboxylate (6) is removed from the reaction system, the carbonate ester (4) is removed from the reaction system. Therefore, when the boiling point of the carbonate ester (4) is lower than that of the carboxylate (6), it is desired to use a combination of the batch reactor and the vapor-liquid contacting reactor or a combination of the flow reactor and the vapor-liquid contacting reactor. More specifically, first, a transesterification reaction is carried out to a degree, more preferably, the second-step reaction proceeds to substantially equilibrium state in the batch reactor or the flow reactor beforehand so as to convert a substantial amount of the carbonate ester (4) to carbonate monoester and carbonate diester. Next, the reaction liquid is supplied to the vapor-liquid contacting reactor to perform vapor-liquid contacting, i.e., reaction distillation while further proceeding the second-step reaction, thereby continuously removing the carboxylate (6) from the reaction system. This makes the removal of the carbonate ester (4) from the reaction system difficult, thereby further improving the reaction efficiency.

In the process for preparing carbonate esters according to the present invention, transesterification between the carboxylate (1) and an aromatic hydroxy compound is performed in the presence of a catalyst (first-step reaction). Additionally, transesterification between the carboxylate (3) and the carbonate ester (4) is carried out in the presence of a catalyst (second-step reaction). The catalyst used in the first-step reaction and the catalyst used in the second-step reaction may be the same or different from each other.

Examples of the catalysts are: mineral acids such as sulphuric acid; sulfonic acids such as paratoluenesulfonic acid; solid acids such as ion exchange resins and zeolite; base such as sodium hydroxide; metal alkoxide such as tetraisopropoxide titanate, zirconium(IV) isopropoxide;

Lewis acid such as aluminum chloride and titanium tetrachloride, and compounds producing Lewis acid; metal phenoxides such as lead phenoxide and phenoxytitanium; lead oxides; lead salts such as carbonates; metal acetylacetonate complex such as zirconium(IV) acetylacetonate, bis(acetylacetonato) copper (II), zinc(II) acetylacetonate and lithium acetylacetonate; organotin compounds such as dibutyltin oxide; titanium silicate; and metal-substituted aluminum phosphate. It is also possible to use typical proton acid, proton base, solid acid and solid base as catalysts. Among the listed catalysts, weak acid and weak base are more preferred because they improve the selectivity of the carboxylate (5).

When using a solid heterogeneous catalyst, it is necessary to bring the reaction liquid into contact with the catalyst while maintaining the catalyst inside the reactor. When using a packed column or a complex distillation column as a reactor, it is possible to fill the solid catalyst to replace a part or all of the packings packed in the column.

When using a homogeneous catalyst, a mixed solution containing the catalyst is supplied into the reactor. For example, when using a distillation column as a reactor, it is possible to supply the catalyst by mixing it with at least one of the carboxylate (1), the carbonate ester (4) and an aromatic hydroxy compound. In this case, it is also possible to supply the mixed solution containing the catalyst to a stage of the distillation column to which the carboxylate (1), the carbonate ester (4) or the aromatic hydroxy compound is supplied, or to a different stage. In the distillation column, when the number of regions (stages) in which catalysts are present is increased, the contact frequency of the reaction liquid and the catalyst is increased and satisfactory reaction efficiency is achieved. It is therefore desirable to supply the catalyst to higher stages of the distillation column. For example, when a bubble column is used as the reactor, it is possible to supply the catalyst from an upper portion of the bubble column by mixing it with a raw material having a higher boiling point. It is also possible to maintain the catalyst inside the bubble column and bring the reaction liquid into contact with the catalyst. When the homogeneous catalyst is used and when separation and removal of the catalyst are not performed after the completion of the first-step reaction, it is desirable to use the same catalyst for both the first-step reaction and the second-step reaction.

In the first-step reaction, when the homogeneous catalyst is used with a reactor other than a fixed-bed type reactor, the minimum catalyst concentration is 0.1 ppm, preferably 1 ppm, and more preferably 10 ppm, based on the total amount of carboxylate (1) and the aromatic hydroxy compound as raw materials. The maximum catalyst concentration up to which the catalyst dissolves in a saturated state in the reaction liquid in the reactor is about 10 weight percent, preferably 5 weight percent, and more preferably 1 weight percent. When the heterogeneous catalyst is used with a reactor such as a batch reactor and a suspension-bed type reactor, the minimum amount of the catalyst is 0.1 weight percent, preferably 0.5 weight percent, and more preferably 1 weight percent. In this case, the maximum amount of the catalyst is 40 weight percent, preferably 30 weight percent, and more preferably 20 weight percent.

In the second-step reaction, when a reactor other than a fixed-bed type reactor is used, the minimum catalyst concentration is 0.1 ppm, preferably 1 ppm, and more preferably 10 ppm, based on the total amount of the carboxylate (3) and the carbonate ester (4) as raw materials. The maximum catalyst concentration up to which the catalyst dissolves in a saturated state in the reaction liquid in the reactor is about 10 weight percent, preferably 5 weight percent, and more preferably 3 weight percent. When the heterogeneous catalyst is used with a reactor such as a batch reactor and a suspension-bed type reactor, the minimum amount of the catalyst is 0.1 weight percent, preferably 0.5 weight percent, and more preferably 1 weight percent. In this case, the maximum amount of the catalyst is 40 weight percent, preferably 30 weight percent, and more preferably 20 weight percent.

The method for supplying the raw materials to the reactor is not particularly limited. Therefore, a mixture of the carbonate ester (4), the aromatic hydroxy compound and the carboxylates (1) and (3) may be supplied, or the carbonate ester (4), the aromatic hydroxy compound and the carboxylates (1) and (3) may be separately supplied. It is possible to supply the carbonate ester (4), the aromatic hydroxy compound and the carboxylate (1) in liquid form, gaseous form, or vapor-liquid mixed form. However, for example, if the reactor is a multistage distillation column, in order to smoothly perform contacting of these compounds in the reactor, it is desirable that a high boiling point raw material is supplied to a higher stage than a stage to which a low boiling point raw material is supplied. The high boiling point raw material may include a part of the low boiling point raw material, and the low boiling point raw material may include a part of the high boiling point raw material.

Although the mole ratio of the carboxylate (1) and the aromatic hydroxy compound in the first-step reaction is varied depending on the type and amount of a catalyst to be used and reaction conditions, it is preferably in a range of from 1:100 to 100:1, more preferably in a range of from 1:50 to 50:1, still more preferably in a range of from 1:20 to 20:1, and most preferably in a range of from 1:5 to 5:1. As described above, the first-step reaction is an equilibrium reaction which is extremely biased to the original system. Therefore, by using one of the carboxylate (1) and the aromatic hydroxy compound excessively, the reaction efficiency (equilibrium conversion) of the other is increased. However, if the mole ratio thereof is out of the above-mentioned ranges, the excessively used carboxylate (1) or aromatic hydroxy compound needs to be collected and recycled. Thus, this is industrially disadvantageous and undesirable.

In the second-step reaction, the mole ratio of the carboxylate (3) and the carbonate ester (4) is varied depending on the type and amount of a catalyst to be used, but it is preferably in a range of from 1:100 to 100:1, more preferably in a range of from 1:50 to 50:1, still more preferably in a range of from 1:20 to 20:1, yet more preferably in a range of from 1:10 to 10:1, and most preferably in a range of from 1:5 to 5:1. By using one of the carboxylate (1) and the carbonate ester (4) excessively, the reaction efficiency (equilibrium conversion) of the other is increased. However, if the mole ratio thereof is out of the above-mentioned ranges, the excessively used carboxylate (3) or carbonate ester (4) needs to be collected and recycled. Thus, this is industrially disadvantageous and undesirable.

In the second-step reaction, the reaction system may include the carboxylate (1) and the aromatic hydroxy compound as unreacted compounds which have not reacted in the first-step reaction. However, when the amount of the unreacted compounds is relatively large, it is desirable to separate and collect the unreacted compounds before performing the second-step reaction. The collected unreacted compounds are reusable as raw materials in the first-step reaction. In order to efficiently produce the carbonate ester (5), the content of the carboxylate (3) in the total amount of the carboxylate (3), the carboxylate (1) and the aromatic hydroxyl compound is preferably not lower than 10 mole percent, more preferably not lower than 20 mole percent, and still more preferably not lower than 30 mole percent.

When operating the reactor, factors determining the operating conditions are, for example, the operating temperature (reaction temperature), the operating pressure, the residence time of liquid, the amount of hold-up liquid and so on. When the reactor is a distillation column, the number of stages and the reflux ratio, etc. are added to the operating conditions. When the reactor is a flow reactor, the liquid hourly space velocity (LHSV) is further added to the operating conditions. The liquid hourly space velocity is given by a value obtained by dividing the volume flow rate of the raw materials flowing in the reactor by the volume of the reactor.

In the first-step reaction, although the operating temperature is varied depending on the types of the carboxylate (1) and the aromatic hydroxy compound, the type and amount of the catalyst and other conditions (factors), the minimum operating temperature is 50° C., preferably 100° C., more preferably 140° C., and still more preferably 160° C. The maximum operating temperature is 350° C., and preferably 300° C.

In the second-step reaction, the operating temperature is varied depending on the types of the carboxylate (3) and the carbonate ester (4), the type and amount of the catalyst and other conditions (factors), but the minimum operating temperature is 50° C., preferably 100° C., more preferably 140° C., and still more preferably 160° C. The maximum operating temperature is 350° C., preferably 300° C., and more preferably 280° C.

When the operating temperature is lower than 50° C., since the catalytic activity is decreased, the reaction time becomes longer and the productivity is lowered, giving unfavorable results. On the other hand, when the operating temperature is higher than 350° C., the following unfavorable results are given. Namely, side reactions such as the production of ethers (such as diaryl ethers and alkyl aryl ethers) by a dehydrating reaction or a decarbonating reaction are likely to occur, and the pressure inside the reactor is excessively increased.

The operating pressure is a reduced pressure, normal pressure or increased pressure. Although the operating pressure is varied depending on the types of the carboxylates (1) and (3), the aromatic hydroxy compound and the carbonate ester (4), the type and amount of the catalyst, and other conditions (factors), it is preferably in the range of from 1 mmHg to 100 kg/cm$^2$, and more preferably in the range of from 5 mmHg to 50 Kg/cm$^2$.

The amount of hold-up liquid and the number of stages are closely related to the reaction time, i.e., the residence time. Namely, in order to improve the equilibrium conversion, it is necessary to increase the residence time to a degree. In order to increase the residence time, it is necessary to increase the amount of hold-up liquid or the number of stages. Although increasing the amount of hold-up liquid is more preferred, if the amount of hold-up liquid becomes larger than a certain amount, flooding occurs. Therefore, the amount of hold-up liquid with respect to the capacity (volume) of an empty column of the reactor, i.e., the volume ratio of the hold-up liquid to the empty column is preferably in the range of from 0.005 to 0.75, and more preferably in the range of from 0.01 to 0.5. When increasing the number of stages, considering the manufacturing cost of the reactor, height restriction, and costs for service and installation, a preferred number of stages is between around 2 and 100. When the number of stages is increased, if the difference in the boiling point between the carboxylate (1) and the by-produced alcohol is relatively small in the first-step reaction, and if the difference in the boiling point between the carboxylate (3) and the carbonate monoester or the by-produced carboxylate (6) is relatively small in the second-step reaction, the vapor-liquid separation efficiency is improved.

In the first-step reaction, the reflux ratio is preferably in the range of from 0 to 100, more preferably in the range of from 0 to 50, and still more preferably in the range of from 0 to 25. In the second-step reaction, the reflux ratio is preferably in the range of from 0 to 100, more preferably in the range of from 0 to 50, still more preferably in the range of from 0 to 25, and most preferably in the range of from 0.1 to 25. When the carboxylate (1) and the by-produced alcohol form an azeotrope in the first-step reaction, the reflux ratio is preferably zero or chosen from relatively small values. When the difference in boiling point between the carboxylate (1) and the by-produced alcohol is relatively small, the reflux ratio is preferably selected from relatively large values. Similarly, when the difference in boiling point between the carboxylate (3) and the carbonate monoester or the by-produced carboxylate (6) is relatively small in the second-step reaction, the reflux ratio is preferably selected from relatively large values so as to sufficiently proceed the reaction.

The liquid hourly space velocity (LHSV) is varied depending on the types of the carboxylate (1), the aromatic hydroxy compound and the carbonate ester (4), the type and amount of the catalyst, the operating temperature, and other conditions (factors). However, the minimum liquid hourly space velocity is 0.05 hr$^{-1}$, preferably 0.1 hr$^{-1}$, and more preferably 0.2 hr$^{-1}$, while the maximum liquid hourly space velocity is 50 hr$^{-1}$, and preferably 20 hr$^{-1}$.

When a batch reactor is used as the reactor, predetermined amounts of the carboxylate (1), the aromatic hydroxy compound, the carbonate ester (4) and the catalyst are fed to the reactor, and the first-step reaction and/or the second-step reaction is performed at a predetermined reaction temperature while stirring the compounds. Although the reaction pressure is given by the sum of the vapor pressure of each of the compounds, it is possible to pressurize the reactor by introducing an inert gas (such as nitrogen) to the reaction system. The reaction time is varied depending on the type and amount of the catalyst, the reaction temperature and so on, but is preferably in the range of from around 0.01 to 100 hours, and more preferably in the range of from 0.1 to 50 hours.

When a heterogeneous catalyst is used, after the completion of the reaction, the heterogeneous catalyst is easily removed and collected from the reaction liquid by using known methods, for example, a centrifugal method and filtration. When a homogeneous catalyst is used, after the completion of the reaction, the homogeneous catalyst is easily separated and collected from the reaction liquid by using known methods, for example, distillation. When the same homogeneous catalyst is used for both the first-step reaction and the second-step reaction, it is possible to start the second-step reaction without separating the catalyst after the completion of the first-step reaction.

By separating the catalyst after the completion of the second-step reaction using the above-mentioned method, and by using known methods such as distillation, extraction and recrystallization, the carbonate ester (5), i.e., carbonate diester as an object is easily isolated. Moreover, the carboxylate (6) and carbonate monoester as by-products, and the carbonate ester (4), aromatic hydroxy compound and so on as unreacted compounds are easily separated and collected, if necessary.

In the process for preparing carbonate esters according to the present invention, a solvent may be added to the reaction system, i.e., the reaction liquid, if necessary. As for a solvent to be added for easing the reaction operation, compounds inert to the reaction system are used. Examples of such compounds are ethers, aliphatic hydrocarbon, aromatic hydrocarbon, and halogenated hydrocarbon. When carboxylate (1) and the by-produced alcohol form an azeotrope in the first-step reaction, the presence of a solvent, which forms an azeotrope whose azeotropic point is lower than that of the above-mentioned azeotrope together with the alcohol, in the reaction system is preferred. For example, when the alcohol is methanol, preferred solvents are compounds such as benzene and cyclohexane. The solvent forms an azeotrope of a relatively low azeotropic boiling point together with methanol. Since the formation of an azeotrope between the carboxylate (1) and methanol is limited, the carboxylate (1) and methanol are easily separated, thereby improving the equilibrium conversion. Moreover, even when the carboxylate (1) and methanol do not form an azeotrope, in order to facilitate the separation thereof, a solvent which forms an azeotrope of a low azeotropic point together with the alcohol may be present in the reaction system.

In order to easily remove the alcohol and the carboxylate (6) from the reaction system, a gas (nitrogen) inert to the reaction system may be introduced from the lower portion of the reactor.

In the second-step reaction, when the boiling point of the carbonate ester (4) is relatively low, it is desirable to perform a transesterification reaction using a combination of the flow reactor and the vapor-liquid contacting reactor. More specifically, first, the transesterification reaction is carried out to a degree beforehand using the flow reactor so as to convert a substantial amount of the carbonate ester (4) to the carbonate ester (5). Then, this reaction liquid is supplied to the vapor-liquid contacting reactor to perform vapor-liquid contacting while further proceeding the transesterification reaction, i.e., performing reaction distillation. Consequently, the carboxylate (6) is continuously removed from the reaction system. As a result, the removal of the carbonate ester (4) from the reaction system becomes difficult, achieving further improved reaction efficiency.

In this case, the operating conditions for the flow reactor are varied depending on the types of the carboxylate (3) and the carbonate ester (4), the type and amount of the catalyst, and other conditions (factors). However, the reaction temperature is preferably in the range of from 50° C. and 350° C., and more preferably in the range of from 100° C. and 280° C. The reaction pressure is usually not lower than atmospheric pressure at the above-mentioned reaction temperature. However, the reaction pressure needs to be not lower than the vapor pressure of the reaction liquid, and preferably not higher than 100 kg/cm$^2$. The reaction time is varied depending on the type and amount of the catalyst and the reaction temperature, but is preferably in the range of from 0.01 to 50 hours, and more preferably in the range of from 0.1 to 20 hours. It is desirable to bring the conversion of the carboxylate (3) or the carbonate ester (4) close to the equilibrium conversion of the transesterification reaction. Namely, in the flow reactor, it is desirable to proceed the transesterification reaction until a substantially equilibrium state is obtained. However, in order to proceed the transesterification reaction until the substantially equilibrium state is obtained, it is necessary to increase the reaction time to a degree. Thus, in order to efficiently prepare the carbonate ester (5), it is necessary to carry out the transesterification reaction in the flow reactor by at least 10 percent of the equilibrium conversion of the transesterification reaction, preferably at least 20 percent, and still more preferably at least 40 percent.

The following description discusses a process for preparing the carbonate ester (5) using the carboxylate (1), the aromatic hydroxy compound and the carbonate ester (4) as raw materials.

First, an example of the process for preparing carbonate esters using a reaction device having a batch reactor as a reactor will be discussed with reference to FIG. 1.

As illustrated in FIG. 1, the reaction device includes a batch reactor 1 as a reactor, a distillation column 2, a condenser 5, and a pump 6.

The batch reactor 1 performs a transesterification between the carboxylate (1) and the aromatic hydroxy compound, and a transesterification between the produced carboxylate (3) and the carbonate ester (4). The batch reactor 1 is pressure resistant, and includes a stirring device 1a and a heating device 1b. A feed pipe 10 is connected to the batch reactor 1. Also connected to the bottom of the batch reactor 1 is an outlet pipe 11. The distillation column 2 is installed on the top of the batch reactor 1. The outlet pipe 11 enables the removal of the reaction liquid in the batch reactor 1 from the reaction system.

The distillation column 2 continuously distillates off a low boiling point component containing the alcohol or carboxylate (6) as a by-product from the reaction system. The bottom of the distillation column 2 is connected to the top of the batch reactor 1, while the top of the distillation column 2 is connected to the condenser 5 through a conduit 13.

The condenser 5 condenses the distillate of the distillation column 2 into a liquid phase. The condenser 5 is connected to the top of the distillation column 2 through the conduit 13, and connected to the pump 6 through a conduit 14. The condenser 5 includes a regulating pipe 15 provided with a pressure control valve 16. The conduit 14 branches so that a part of the distillate is continuously removed from the reaction system.

The pump 6 refluxes the distillate to the distillation column 2 at a predetermined reflux ratio. The pump 6 is connected to the condenser 5 through the conduit 14, and connected to the top of the distillation column 2 through a conduit 17.

Next, an example of the process for preparing carbonate esters using the reaction device having the above-mentioned structure is explained below.

First, a first-step reaction is carried out to produce the carboxylate (3). More specifically, a mixture containing the carboxylate (1), an aromatic hydroxy compound, a catalyst and, if necessary, a solvent is introduced into the batch reactor 1 through the feed pipe 10. Second, the mixture is heated while stirring. Then, a transesterification between the carboxylate (1) and the aromatic hydroxy compound is performed in the presence of the catalyst at a predetermined temperature.

Next, a low boiling point component containing the by-produced alcohol is distilled in the distillation column 2 to distill off the alcohol. A gas containing the alcohol is continuously condensed to a distillate by the condenser 5. A part of the distillate is refluxed to the top of the distillation column 2 through the pump 6 at a predetermined reflux ratio, while the remaining distillate is continuously removed from the reaction system. Namely, the by-produced alcohol is continuously removed as the distillate from the reaction system.

A low boiling point raw material, for example, the carboxylate (1) may be continuously supplied to the batch reactor 1 through the feed pipe 10 in the course of the first-step reaction. In order to easily distill off the alcohol, the solvent or an inert gas may be continuously supplied to the batch reactor 1 through the feed pipe 10. By setting the number of stages of the distillation column 2 and the reflux ratio to optimum values, it is possible to collect the alcohol with high purity.

After the completion of the first-step reaction, the alcohol, the unreacted carboxylate (1) and the aromatic hydroxy compounds are distilled off. As a result, the produced carboxylate (3) and the catalyst remain in the batch reactor 1. A part of the unreacted carboxylate (1) and of the aromatic hydroxy compound are allowed to remain in the batch reactor 1. After the completion of the first-step reaction, it is also possible to remove the reaction liquid in the batch reactor 1 from the reaction system through the outlet pipe 11 and to distill off the alcohol, the unreacted carboxylate (1) and aromatic hydroxy compound from the reaction liquid using a separate distillation device (not shown). In this case, it is necessary to return the residue product into the batch reactor 1.

Subsequently, a second-step reaction is performed to produce the carbonate ester (5). More specifically, the carbonate ester (4) is introduced into the batch reactor 1 through the feed pipe 10. Next, the reaction liquid is heated while stirring. Then, a transesterification between the carboxylate (3) and the carbonate ester (4) is performed in the presence of the catalyst at a predetermined temperature.

In the second-step reaction, if the boiling point of the carbonate ester (4) is lower than that of the by-produced carboxylate (6), it is desirable to close the batch reactor 1. Specifically, in the closed batch reactor 1, it is desirable to proceed the second-step reaction, preferably, until a substantially equilibrium state is achieved. Thereafter, it is desirable to distill off the by-produced carboxylate (6) and the unreacted carbonate ester (4) using the distillation column 2, and to further proceed the second-step reaction. If the boiling point of the carbonate ester (4) is higher than that of the by-produced carboxylate (6), it is desirable to distill off the carboxylate (6) as the by-product using the distillation column 2 while carrying out the second-step reaction. In this case, it is possible to collect the carboxylate (6) with high purity. When the carboxylate (6) is reusable as the carboxylate (1), the carboxylate (1) is not substantially consumed.

After the completion of the second-step reaction, the carboxylate (6), the unreacted carboxylate (3) and carbonate ester (4) are distilled off. Then, for example, by performing fractionation, carbonate diester as the object is isolated. It is thus possible to easily collect and reuse the catalyst remaining in the batch reactor 1. Additionally, after the completion of the second-step reaction, the reaction liquid in the batch reactor 1 may be removed from the reaction system through the outlet pipe 11, and the carboxylate (6), the unreacted carboxylate (3) and carbonate ester (4) may be distilled off from the reaction liquid using a separate distillation device (not shown). It is also possible to isolate carbonate diester as the object by performing, for example, extraction and recrystallization instead of fractionation.

By performing the above-mentioned reaction operations, the carbonate ester (5) is efficiently produced.

Figure 2:
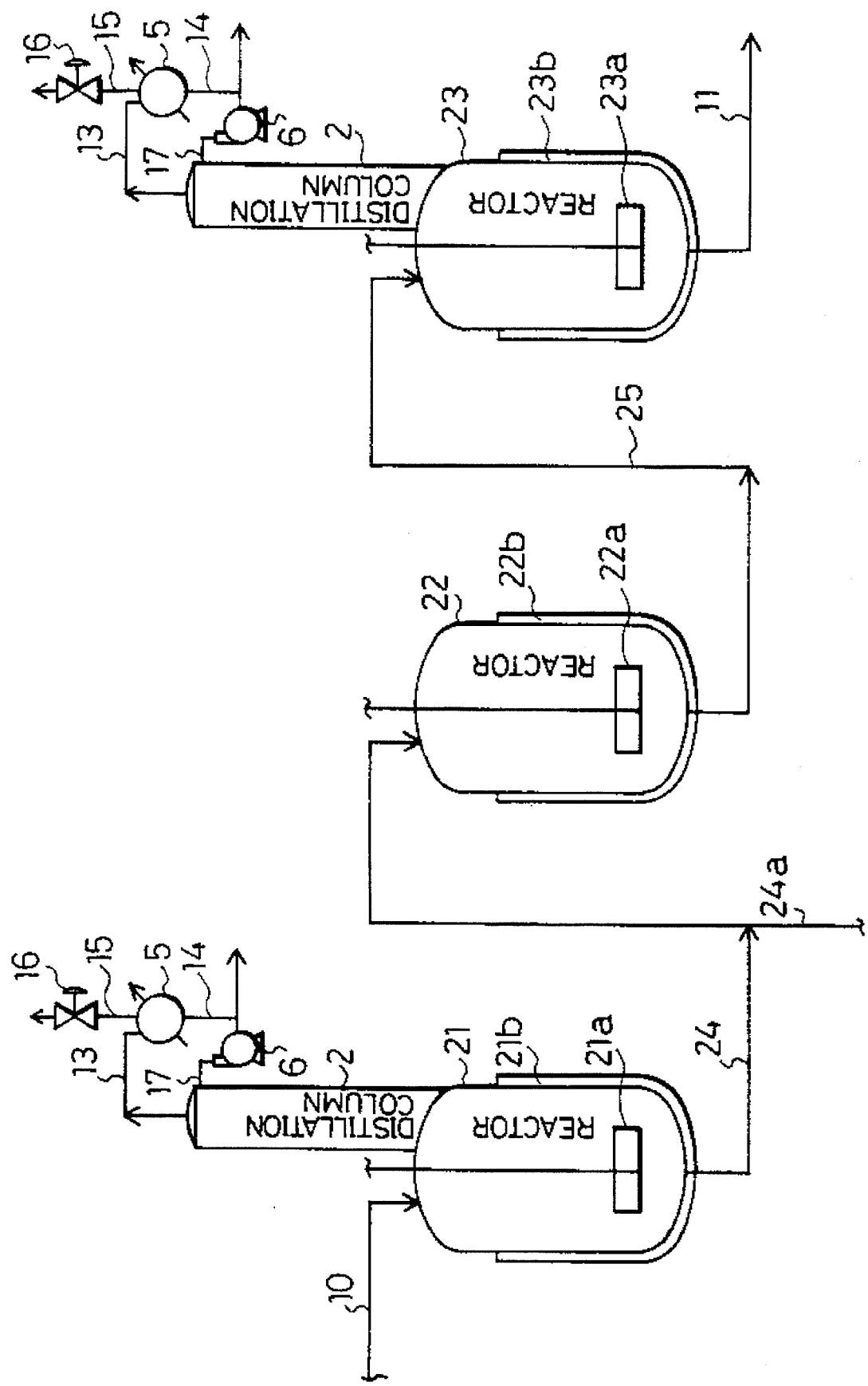

Referring now to FIG. 2, the following description explains an example of the process for preparing carbonate esters using a reaction device having a continuous tank reactor as the reactor. For the sake of explanation, the structures performing the same functions as the structures of the above-mentioned reaction device (shown in FIG. 1) will be designated by the same code and their description will be omitted. In the given example, the boiling point of the carbonate ester (4) is lower than that of the carboxylate (6).

As illustrated in FIG. 2, the reaction device includes reactors 21, 22, 23, the distillation columns 2, the condensers 5, and the pumps 6.

The reactor 21 performs a transesterification between the carboxylate (1) and the aromatic hydroxy compound to produce the carboxylate (3). The reactor 21 includes a stirring device 21a and a heating device 21b. The feed pipe 10 is connected to the reactor 21. Also connected to the bottom of the reactor 21 is a conduit 24. The distillation column 2 is installed on the top of the reactor 21. A conduit 24a is connected to the conduit 24 so as to enable, for example, mixing of the carbonate ester (4) through the conduit 24a and the reaction liquid removed from the reactor 21.

The reactors 22 and 23 perform a transesterification between the carboxylate (3) and the carbonate ester (4). The reactor 22 is capable of being closed. The reactor 22 includes a stirring device 22a and a heating device 22b. The conduit 24 is connected to the reactor 22. Also connected to the bottom of the reactor 22 is a conduit 25. The reactor 23 includes a stirring device 23a and a heating device 23b. The conduit 25 is connected to the reactor 23. Also connected to the bottom of the reactor 23 is the outlet pipe 11. Additionally, the distillation column 2 is installed on the top of the reactor 23. Other structures of the reaction device are the same as those of the above-mentioned reaction device (FIG. 1).

An example of the process for preparing carbonate esters using the reaction device having the above-mentioned structures is explained below. For the sake of explanation, the same operations as in the above-mentioned reaction device (FIG. 1) will be briefly explained.

First, a first-step reaction is carried out to produce the carboxylate (3). More specifically, a mixture containing the carboxylate (1), an aromatic hydroxy compound, a catalyst and, if necessary, a solvent is introduced into the reactor 21 through the feed pipe 10. Then, a transesterification between the carboxylate (1) and the aromatic hydroxy compound is performed at a predetermined temperature, and the by-product such as an alcohol is distilled off.

Subsequently, the carbonate ester (5) is produced by performing a second-step reaction. Specifically, after the completion of the first-step reaction, the reaction liquid in the reactor 21 is moved to the reactor 22 through the conduit 24. In addition, the carbonate ester (4) is mixed with the reaction liquid through the conduit 24a. Thereafter, a transesterification between the carboxylate (3) and the carbonate ester (4) is performed at a predetermined temperature.

In the closed reactor 22, the second-step reaction is continued until a substantially equilibrium state is achieved. Then, the reaction liquid in the reactor 22 is fed to the reactor 23 through the conduit 25. In the reactor 23, the by-produced carboxylate (6) and the unreacted carbonate ester (4) are distilled off using the distillation column 2, and the second-step reaction is further continued.

Upon the completion of the second-step reaction, the carboxylate (6), the unreacted carboxylate (3) and carbonate ester (4) are distilled off. Then, carbonate diester as the object is isolated by, for example, fractionation. It is thus possible to easily collect the catalyst remaining in the reactor 23 for reuse.

By performing the above-mentioned reaction operations, the carbonate ester (5) is efficiently produced. If the boiling point of the carbonate ester (4) is higher than that of the by-produced carboxylate (6), it is not necessary to provide the reactor 22. Moreover, the reaction device may be constructed to have a plurality of the reactors 21, 22, 23. This structure further improves the reaction efficiency (equilibrium conversion). When a plurality of reactors of the same type are provided, these reactors are connected in series.

Figure 3:
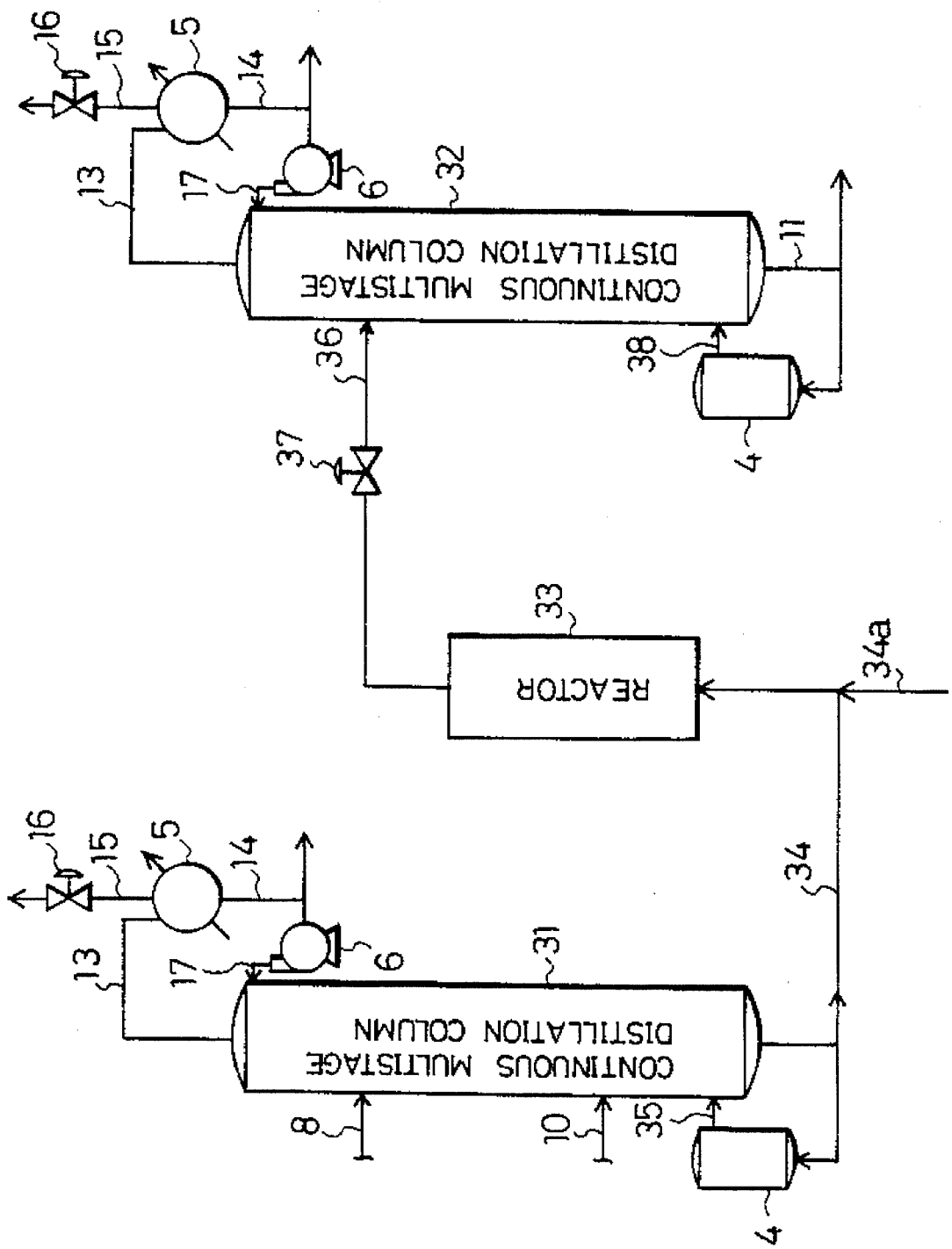

Referring now to FIG. 3, the following description explains an example of the process for preparing carbonate esters using a reaction device having a multistage distillation column as a reactor. For the sake of explanation, the structures performing the same functions as the structures of the above-mentioned reaction device (FIG. 2) will be designated by the same code and their description will be omitted. In the given example, the boiling point of the carbonate ester (4) is lower than that of the carboxylate (6).

As illustrated in FIG. 3, the reaction device includes continuous multistage distillation columns (hereinafter just referred to as the multistage distillation columns) 31 and 32 as reactors, a reactor 33, reboilers 4, the condensers 5, and the pumps 6.

The multistage distillation column 31 carries out vapor-liquid contacting while performing a transesterification between the carboxylate (1) and the aromatic hydroxy compound. Feed pipes 8 and 10 are connected to the multistage distillation column 31. Also connected to the bottom of the multistage distillation column 31 is the reboiler 4 through conduits 34 and 35. The top of the multistage distillation column 31 is connected to the condenser 5 through the conduit 13. In the multistage distillation column 31, the feed pipe 8 is connected to a higher stage than the feed pipe 10. The feed pipe 10 is also allowed to be connected to the bottom of the multistage distillation column 31.

The feed pipe 8 continuously supplies a mixture which contains mainly a compound with a higher boiling point between the carboxylate (1) and the aromatic hydroxy compound to the multistage distillation column 31. The feed pipe 10 continuously supplies a mixture which contains mainly a compound with a lower boiling point between the carboxylate (1) and the aromatic hydroxy compound to the multistage distillation column 31. If there is virtually no difference in the boiling point between the carboxylate (1) and the aromatic hydroxy compound, it is possible to omit either of the feed pipes 8 and 10 and to continuously supply the mixture of the carboxylate (1) and the aromatic hydroxy compound to the multistage distillation column 31.

The reboiler 4 is connected to the bottom of the multistage distillation column 31 through the conduits 34 and 35. The reboiler heats the column bottom liquid withdrawn through the conduit 34, and returns it to the bottom of multistage distillation column 31 through the conduit 35. Namely, the reboiler 4 heats the column bottom liquid for circulation. The conduit 34 branches so that a part of the column bottom liquid as the residue is continuously fed to the reactor 33. Additionally, a conduit 34a is connected to the conduit 34 so as to enable the carbonate ester (4) to be mixed with the residue through the conduit 34a.

The reactor 33 and the multistage distillation column 32 perform a transesterification between the carboxylate (3) and the carbonate ester (4). The reactor 33 is a flow reactor. The conduit 34 is connected to the bottom of the reactor 33, while the conduit 36 is connected to the top of the reactor 33. A pressure control valve 37 is attached to the conduit 36.

The multistage distillation column 32 carries out vapor-liquid contacting while performing a transesterification between the carboxylate (3) and the carbonate ester (4). The conduit 36 is connected to an intermediate stage of the multistage distillation column 32. The bottom of the multistage distillation column 32 is connected to the reboiler 4 through the outlet pipe 11 and a conduit 38. The top of the multistage distillation column 32 is connected to the condenser 5 through the conduit 13. The outlet pipe 11 branches so that a part of the column bottom liquid is continuously removed as the residue from the reaction system. Other structures of the reaction device are the same as those of the above-mentioned reaction device (FIG. 2).

Next, an example of the process for preparing carbonate esters using the reaction device having the above-mentioned structures is explained below. For the sake of explanation, the same operations as in the above-mentioned reaction device (FIG. 2) will be briefly explained.

First, a first-step reaction is carried out to produce the carboxylate (3). More specifically, a mixture containing the carboxylate (1) and a mixture containing an aromatic hydroxy compound are continuously supplied to the multistage distillation column 31 through the feed pipes 8 and 10. Second, vapor-liquid contacting is carried out while performing a transesterification between the carboxylate (1) and aromatic hydroxy compound supplied to the multistage distillation column 31 in the presence of a catalyst. Namely, reaction distillation is performed. In addition, the by-product such as an alcohol is continuously removed as the distillate. When the catalyst is a homogeneous catalyst, the catalyst is continuously supplied together with the carboxylate (1) and/or the aromatic hydroxy compound to the multistage distillation column 31. When the catalyst is a heterogeneous catalyst, the catalyst is retained in the multistage distillation columns 31 and 32 and the reactor 33. Furthermore, when using a solvent, the solvent is continuously supplied to the multistage distillation column 31 through the feed pipe 10. However, it is also possible to separately provide a solvent supply pipe.

Next, the carbonate ester (5) is produced by performing a second-step reaction. Specifically, the residue of the multistage distillation column 31 is continuously fed to the reactor 33 through the conduit 34. In addition, the carbonate ester (4) is continuously mixed with the residue through the conduit 34a. Thereafter, a transesterification between the carboxylate (3) and the carbonate ester (4) is performed at a predetermined temperature.

In the reactor 33, the second-step reaction is continued, preferably, until a substantially equilibrium state is achieved. Thereafter, the reaction liquid in the reactor 33 is continuously supplied to the multistage distillation column 32 through the conduit 36.

In the multistage distillation column 32, the reaction is further continued. Specifically, vapor-liquid contacting is carried out while performing a transesterification between the carboxylate (3) and the carbonate ester (4) supplied to the multistage distillation column 32 in the presence of a catalyst. Namely, reaction distillation is performed. Moreover, the by-produced carboxylate (6), and the unreacted carbonate ester (4) and aromatic hydroxy compound are continuously removed as the distillate.

The distillate is preferably separated into the unreacted carbonate ester (4) and a component containing the carboxylate (6) by using known methods, for example, distillation. The collected carbonate ester (4) is reusable as a raw material for the second-step reaction, while the collected component containing the carboxylate (6) is reusable as a raw material for the first-step reaction. Thus, the carboxylate (1) is not substantially consumed.

The column bottom liquid containing the generated carbonate ester (5) is continuously removed as the residue from the reaction system to the outside of the multistage distillation column 32. Namely, the carbonate ester (5) as the object is continuously removed as the residue from the reaction system. When the catalyst is a homogeneous catalyst, the catalyst is easily separated and collected from the residue using known methods, for example, distillation. By supplying the collected catalyst to the multistage distillation column 31, it is recycled for a reaction.

By performing the above-mentioned reaction operations, the carbonate ester (5) is continuously produced in an efficient manner. If the boiling point of the carbonate ester (4) is higher than that of the by-produced carboxylate (6), it is not necessary to provide the reactor 33. Moreover, when a higher boiling point compound between the carboxylate (3) and the carbonate ester (4) is continuously supplied to a higher stage of the multistage distillation column 32 while continuously supplying a lower boiling point compound to a lower stage, there is no need to provide the reactor 33. Furthermore, if different homogeneous catalysts are used in the first-step reaction and second-step reaction, respectively, it is necessary to connect a separate distillation column in series between the multistage distillation column 31 and the reactor 33. In this case, there is a need to mix the catalyst to be used in the second-step reaction with the reaction liquid through the conduit 34a.

Figure 4:
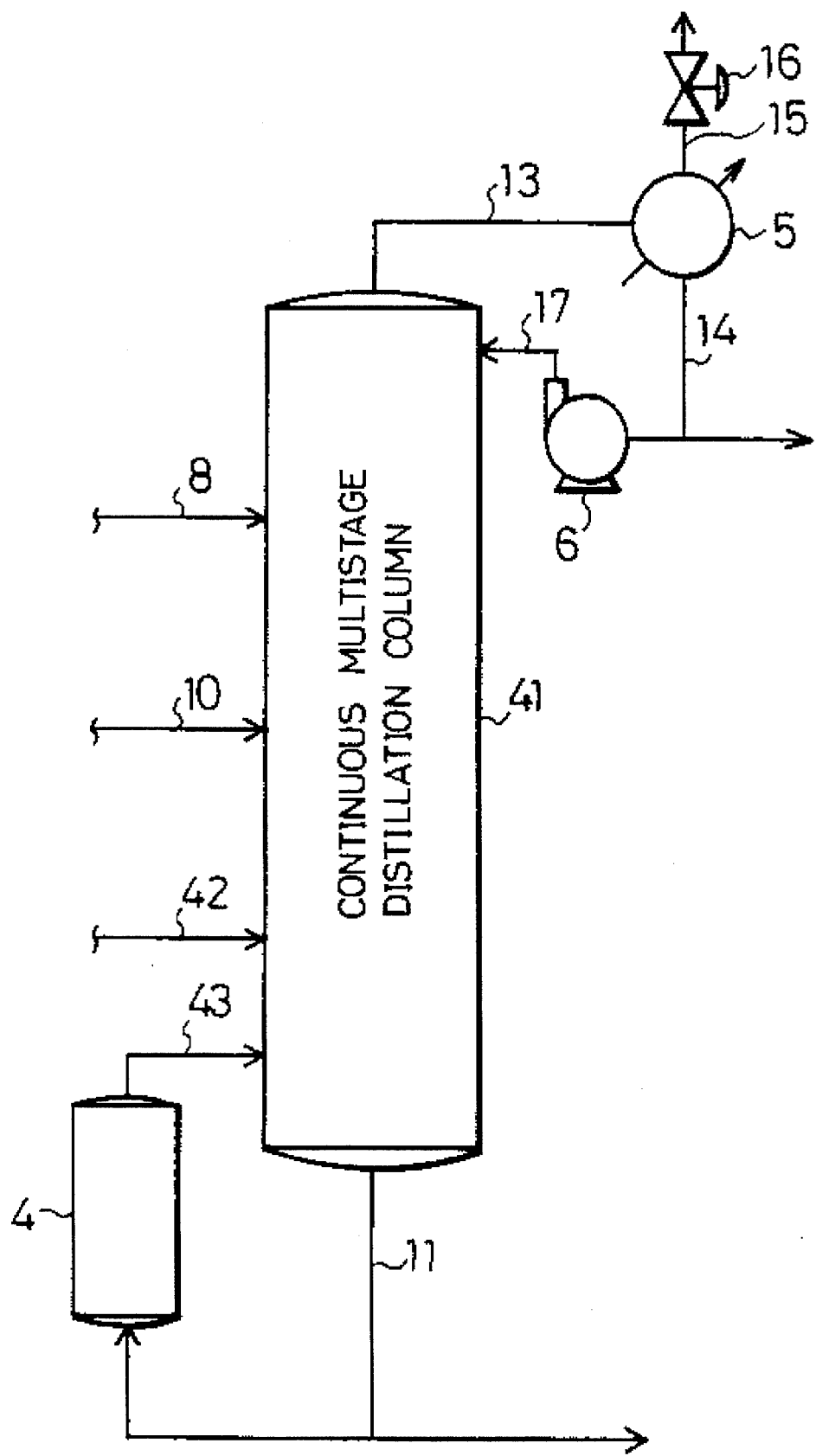

There is no need to restrict the structure of the reaction device having a multistage distillation column as a reactor to the structure shown in FIG. 3. Namely, it is possible to employ various structures. Referring to FIG. 4, the following description explains an example of the process for preparing carbonate esters using another reaction device having a multistage distillation column as a reactor. For the sake of explanation, the structures performing the same functions as the structures of the above-mentioned reaction device (FIG. 3) will be designated by the same code and their description will be omitted. In the given example, the boiling point of the carboxylate (1) is lower than that of the aromatic hydroxy compound.

As illustrated in FIG. 4, the reaction device includes a continuous multistage distillation column (hereinafter just referred to as the multistage distillation columns) 41 as a reactor, the reboiler 4, the condenser 5, and the pump 6.

The multistage distillation column 41 carries out vapor-liquid contacting while performing a transesterification between the carboxylate (1) and the aromatic hydroxy compound, and also carries out vapor-liquid contacting while performing a transesterification between the produced carboxylate (3) and carbonate ester (4). Feed pipes 8, 10, 42 are connected to the multistage distillation column 41. In the multistage distillation column 41, the feed pipe 8 is connected to a higher stage than the feed pipe 10. The feed pipe 10 is connected to a higher stage than the feed pipe 42. The feed pipe 42 may be connected to the bottom of the multistage distillation column 41.

The feed pipe 8 continuously supplies to the multistage distillation column 41 a mixture containing the aromatic hydroxy compound. The feed pipe 10 continuously supplies to the multistage distillation column 41 a mixture containing the carboxylate (1). The feed pipe 42 continuously supplies to the multistage distillation column 41 a mixture containing the carbonate ester (4). If there is virtually no difference in the boiling point between the carboxylate (1) and the aromatic hydroxy compound, it is possible to omit either of the feed pipes 8 and 10.

The bottom of the multistage distillation column 41 is connected to the reboiler 4 through the outlet pipe 11 and the conduit 43, while the top of the multistage distillation column 41 is connected to the condenser 5 through the conduit 13. The outlet pipe 11 branches so that a part of the column bottom liquid is continuously removed as the residue from the reaction system. Other structures of the reaction device are the same as those of the above-mentioned reaction device (FIG. 3).

Next, an example of the process for preparing carbonate esters using the reaction device having the above-mentioned structures is explained. For the sake of explanation, the same operations as in the above-mentioned reaction device (FIG. 3) will be briefly explained.

First, a mixture containing the carboxylate (1), a mixture containing the aromatic hydroxy compound, and a mixture containing the carbonate ester (4) are continuously supplied to the multistage distillation column 41 through the feed pipes 8, 10 and 42.

Then, vapor-liquid contacting is carried out while performing a transesterification between the carboxylate (1) and aromatic hydroxy compound supplied to the multistage distillation column 41 in the presence of a catalyst. Namely, reaction distillation is performed. As a result, a first-step reaction is carried out, and the carboxylate (3) is produced. The carboxylate (3) flows downward in the multistage distillation column 41. In addition, the by-product such as an alcohol is continuously removed as the distillate. When the catalyst is a homogeneous catalyst, the catalyst is continuously supplied together with the carboxylate (1) and/or the aromatic hydroxy compound to the multistage distillation column 41. When the catalyst is a heterogeneous catalyst, the catalyst is retained in the multistage distillation column 41. Furthermore, when using a solvent, the solvent is continuously supplied to the multistage distillation column 41 through the feed pipe 42. However, it is also possible to separately provide a solvent supply pipe.

Next, vapor-liquid contacting is carried out while performing a transesterification between the produced carboxylate (3) and the carbonate ester (4) supplied to the multistage distillation column 41 in the presence of a catalyst. Namely, reaction distillation is performed. As a result, a second-step reaction is carried out, and the carbonate ester (5) is produced. Additionally, the by-produced carboxylate (6) flows upward in the multistage distillation column 41, and is supplied for the first-step reaction.

The column bottom liquid containing the produced carbonate ester (5) is continuously removed as the residue from the reaction system to the outside of the multistage distillation column 41. Namely, the carbonate ester (5) as the object is continuously removed as the residue from the reaction system. When the catalyst is a homogeneous catalyst, the catalyst is easily separated and collected from the residue using known methods, for example, distillation.

By performing the above-mentioned reaction operations, the carbonate ester (5) is continuously produced in an efficient manner. It is also possible to further supply the residue in the multistage distillation column 41 to a separate multistage distillation column, and carry out vapor-liquid contacting while performing a transesterification. With this arrangement, the reaction efficiency (equilibrium conversion) is further improved.

Next, an example of the process for preparing carbonate esters using different reaction devices for a first-step reaction and a second-step reaction is explained. First, a process for continuously preparing the carboxylate (3) by performing the first-step reaction will be discussed.

Figure 5:
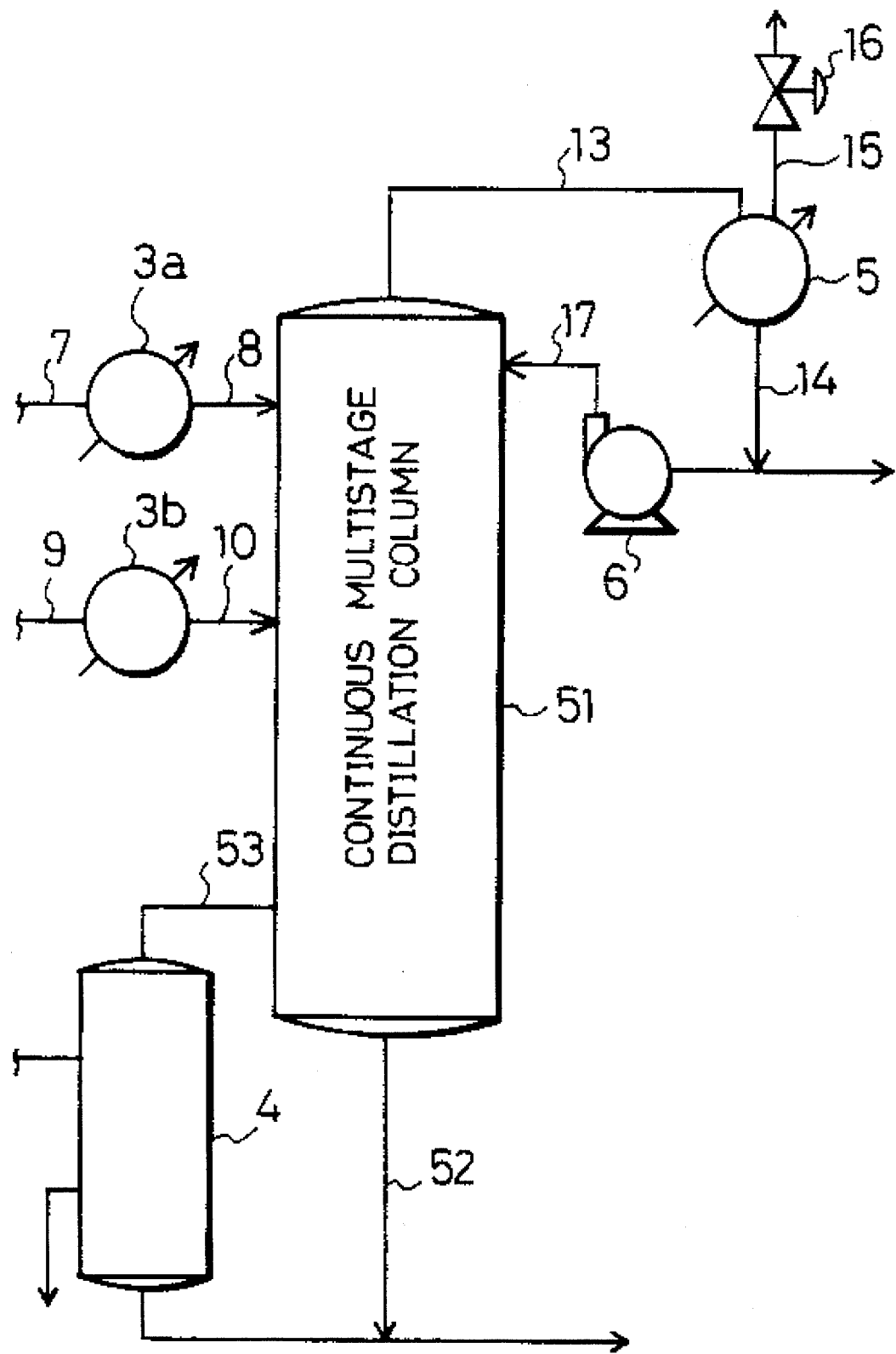

Referring to FIG. 5, the following description explains an example of the process for preparing the carboxylate (3) using a reaction device having a multistage distillation column as a reactor. For the sake of explanation, the structures performing the same functions as the structures of the above-mentioned reaction device (FIG. 4) will be designated by the same code and their description will be omitted. In the given example, the boiling point of the aromatic hydroxy compound is higher than that of the carboxylate (1).

As illustrated in FIG. 5, the reaction device includes a continuous multistage distillation column (hereinafter just referred to as the multistage distillation column) 51 as a reactor, preheaters 3a and 3b, the reboiler 4, the condenser 5 and the pump 6.

The multistage distillation column 51 carries out vapor-liquid contacting while performing a transesterification between the carboxylate (1) and the aromatic hydroxy compound. The multistage distillation column 51 is connected to the preheater 3a through the feed pipe 8, and also to the preheater 3b through the feed pipe 10. The bottom of the multistage distillation column 51 is connected to the reboiler 4 through conduits 52 and 53. The top of the multistage distillation column 51 is connected to the condenser 5 through the conduit 13. In the multistage distillation column 51, the feed pipe 8 is connected to a higher stage than the feed pipe 10. The conduit 52 branches so that a part of the column bottom liquid is continuously removed as the residue from the reaction system. The condenser 5 condenses the distillate of the multistage distillation column 51 into a liquid phase.

The preheater 3a preheats a mixture of a raw material containing a larger amount of aromatic hydroxy compound and a catalyst (hereinafter just referred to as the aromatic hydroxy compound). The preheater 3a is connected to a feed tank (not shown) through a feed pipe 7, and to the multistage distillation column 51 through the feed pipe 8.

The preheater 3b preheats a raw material containing a larger amount of carboxylate (1) (hereinafter just referred to as the carboxylate (1)). The preheater 3b is connected to a feed tank (not shown) which is different from the above-mentioned feed tank through a feed pipe 9, and to the multistage distillation column 51 through the feed pipe 10.

Next, an example of the process for preparing the carboxylate (3) using the reaction device having the above-mentioned structures is explained. For the sake of explanation, the same operations as in the above-mentioned reaction device (FIG. 4) will be briefly explained.

First, the aromatic hydroxy compound is continuously supplied from the feed tank to the multistage distillation column 51 through the feed pipe 7, the preheater 3a and the feed pipe 8. Meanwhile, the carboxylate (1) is continuously supplied from another feed tank to the multistage distillation column 51 through the feed pipe 9, the preheater 3b and the feed pipe 10. Vapor-liquid contacting is carried out while performing a transesterification between the carboxylate (1) and aromatic hydroxy compound supplied to the multistage distillation column 51 in the presence of a catalyst. Namely, reaction distillation is performed.

Then, the column bottom liquid containing the produced carboxylate (3) is continuously removed from the multistage distillation column 51. Namely, the carboxylate (3) is continuously removed as the residue from the reaction system. On the other hand, a gas containing the by-produced alcohol is continuously condensed by the condenser 5, and removed as the distillate from the reaction system. In short, the by-produced alcohol is continuously removed as the distillate from the reaction system.

By performing the above-mentioned reaction operations, the carboxylate (3) is continuously produced in an efficient manner.

Figure 6:
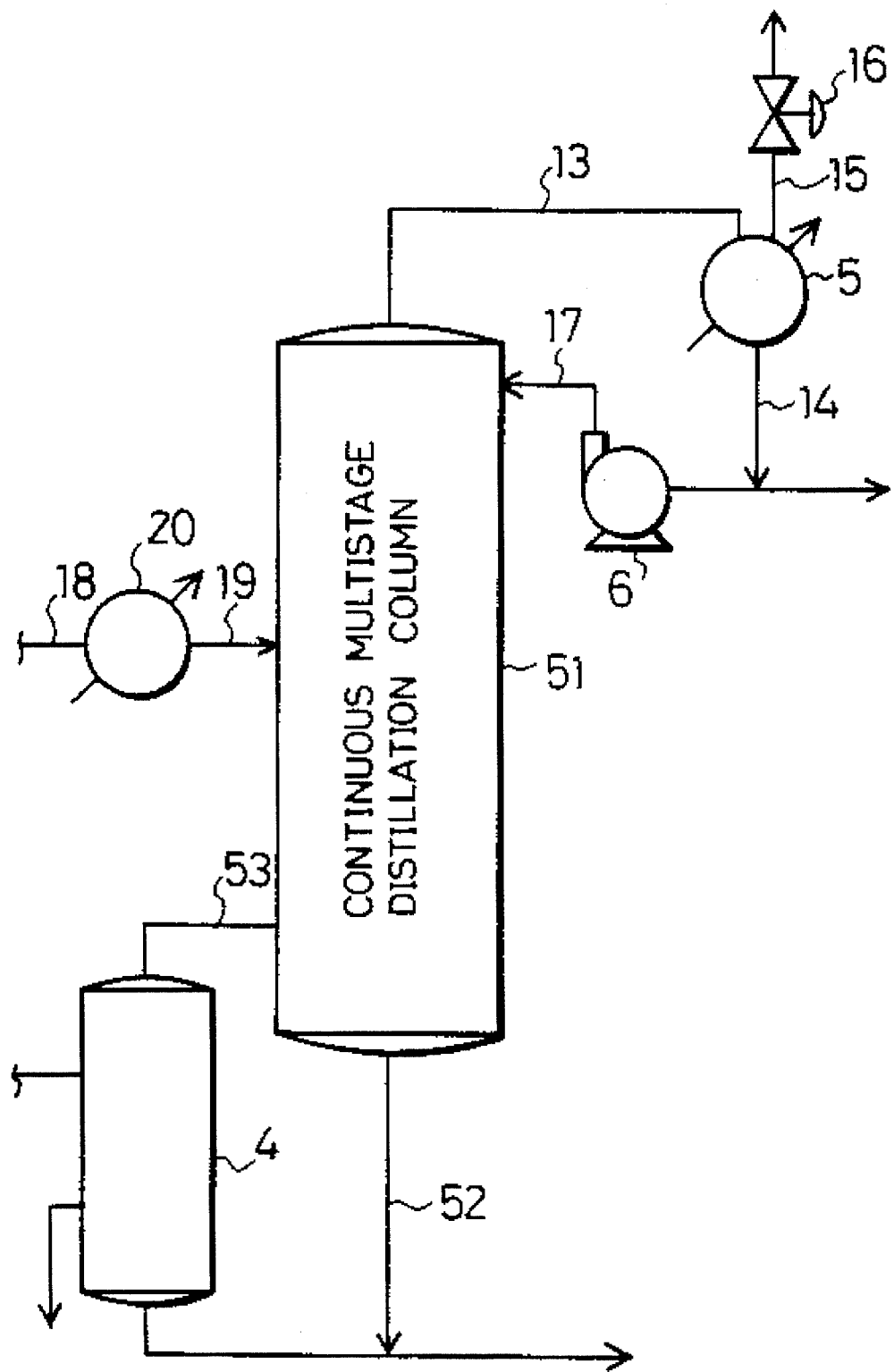

There is no need to restrict the structure of the reaction device used for the first-step reaction to the structure shown in FIG. 5. Namely, it is possible to employ various structures. For example, as illustrated in FIG. 6, the reaction device may include a feed tank (not shown) for supplying a mixture of the carboxylate (1), the aromatic hydroxy compound and the catalyst, a preheater 20, a feed pipe 18 and a feed pipe 19 instead of the feed tanks which separately supply the carboxylate (1) and the aromatic compound, and the preheaters 3a and 3b (FIG. 5).

Figure 7:
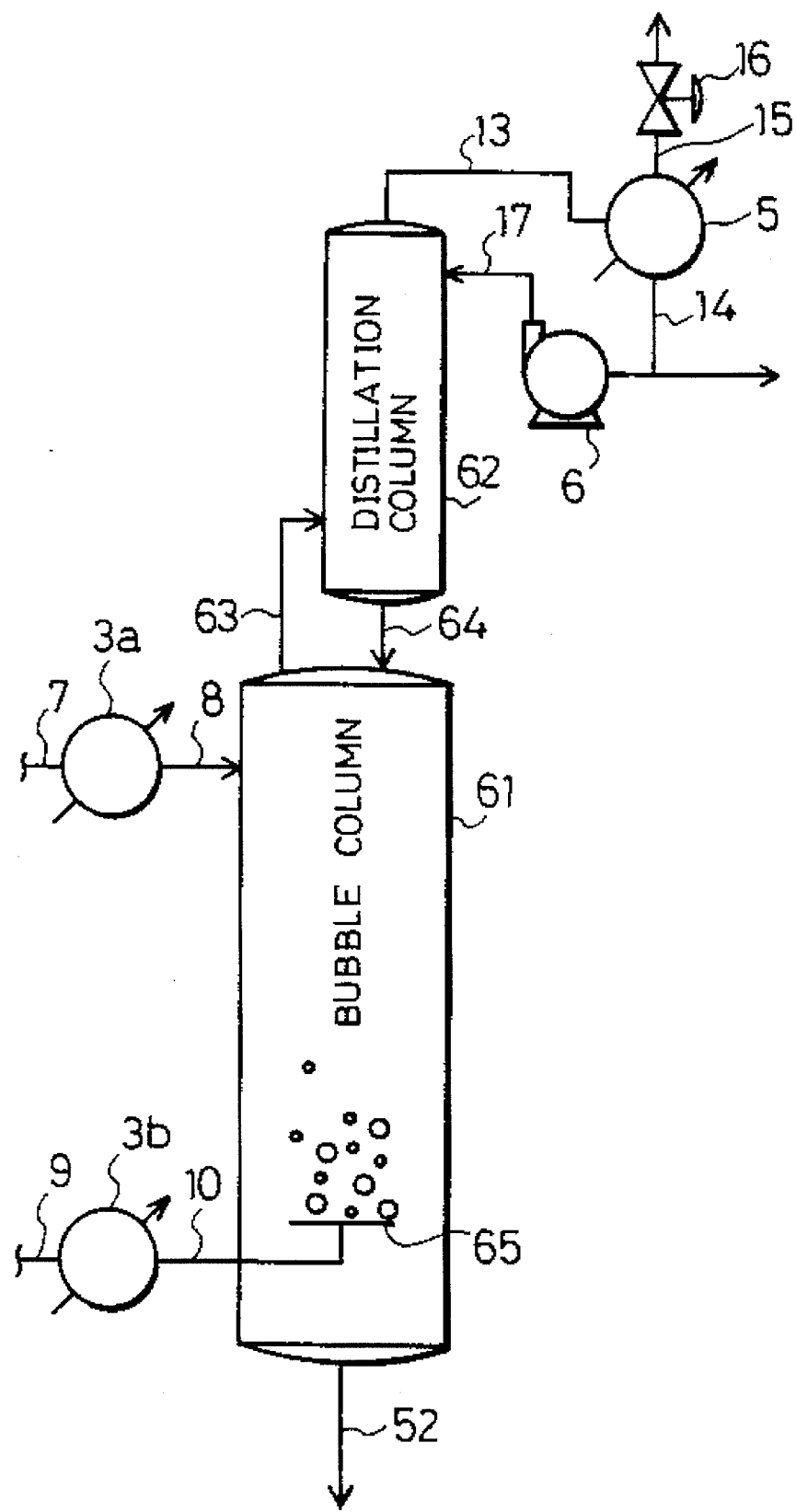

Moreover, as illustrated in FIG. 7, the reaction device may include a bubble column 61 and a distillation column 62 as reactors instead of the multistage distillation column 51 (FIG. 5). The following description explains a reaction device including a bubble column. For the sake of explanation, the structures performing the same functions as the structures of the above-mentioned reaction device (FIG. 5) will be designated by the same code and their description will be omitted.

The bubble column 61 carries out vapor-liquid contacting while performing a transesterification between the carboxylate (1) and the aromatic hydroxy compound. The bubble column 61 is connected to the preheater 3a through the feed pipe 8, and also to the preheater 3b through the feed pipe 10. The bottom of the bubble column 61 is connected to a conduit 52. The top of the bubble column 61 is connected to a distillation column 62 through conduits 63 and 64. The feed pipe 8 is connected to a portion near the top of the bubble column 61, while the feed pipe 10 is connected to a portion near the bottom thereof. A redistributor 65 such as a perforated plate and a porous plate is mounted on an end of the feed pipe 10, which is inserted into the bubble column 61.

The distillation column 62 separates an alcohol from the reaction liquid. The distillation column 62 is connected to the bubble column 61 through the conduits 63 and 64. The distillation column 62 is also connected to the condenser 5 through the conduit 13. A reaction liquid containing a large amount of alcohol is continuously supplied from the bubble column 61 to the distillation column 62 through the conduit 63. On the other hand, the residue is refluxed to the bubble column 61 from the distillation column 62 through the conduit 64. The condenser 5 condenses the distillate of the distillation column 62 into a liquid phase.

The preheater 3b preheats the carboxylate (1) into a gaseous phase. Other structures of the reaction device are the same as those of the above-mentioned reaction device (FIG. 5).

Next, an example of the process for preparing the carboxylate (3) using the reaction device having the above-mentioned structures is explained below. For the sake of explanation, the same operations as in the above-mentioned reaction device (FIG. 5) will be briefly explained.

First, the aromatic hydroxy compound is continuously supplied to the bubble column 61 through the feed pipe 8, while the carboxylate (1) is continuously supplied to the bubble column 61 through the feed pipe 10. Vapor-liquid contacting is carried out while performing a transesterification between the carboxylate (1) and aromatic hydroxy compound supplied to the bubble column 61 in the presence of a catalyst. Namely, reaction distillation is performed.

Then, the column bottom liquid containing the produced carboxylate (3) is continuously removed from the bubble column 61. Namely, the carboxylate (3) is continuously removed as the residue from the reaction system. On the other hand, a reaction liquid containing a large amount of alcohol is continuously supplied to the distillation column 62. The reaction liquid supplied to the distillation column 62 is continuously distilled, and the residue is refluxed to the bubble column 61. Meanwhile, a gas containing the by-produced alcohol is continuously condensed to a distillate by the condenser 5. Namely, the by-produced alcohol is continuously removed as the distillate from the reaction system.

By performing the above-mentioned reaction operations, the carboxylate (3) is continuously produced in an efficient manner.

The following description explains a process for continuously preparing the carbonate ester (5) by performing a second-step reaction.

First, an example of the process for continuously preparing the carbonate ester (5) using the reaction device shown in FIG. 5 is explained. In the given example, the boiling point of the carboxylate (3) is higher than that of the carbonate ester (4).

The multistage distillation column 51 used for the second-step reaction carries out vapor-liquid contacting while performing a transesterification between the carboxylate (3) and the carbonate ester (4). The preheater 3a preheats a mixture of a raw material containing a larger amount of the carboxylate (3) and a catalyst (hereinafter just referred to as the carboxylate (3)). The preheater 3b preheats a raw material containing a larger amount of the carbonate ester (4) (hereinafter just referred to as the carbonate ester (4)).

Next, an example of the process for preparing the carbonate ester (5) using the reaction device having the above-mentioned structures is explained below.

First, the carboxylate (3) is continuously supplied to the multistage distillation column 51 through the feed pipe 8, and the carbonate ester (4) is continuously supplied to the multistage distillation column 51 through the feed pipe 10. Vapor-liquid contacting is carried out while performing a transesterification between the carboxylate (3) and carbonate ester (4) supplied to the multistage distillation column 51 in the presence of a catalyst. Namely, reaction distillation is performed.

Then, the column bottom liquid containing the produced carbonate ester (5) is continuously removed from the multistage distillation column 51. Namely, the carbonate ester (5) is continuously removed as the residue from the reaction system. On the other hand, a gas containing the by-produced carboxylate (6) is continuously condensed to a distillate by the condenser 5. In short, the by-produced carboxylate (6) is continuously removed as the distillate from the reaction system.

By performing the above-mentioned reaction operations, the carbonate ester (5) is continuously produced in an efficient manner.

There is no need to restrict the structure of the reaction device used for the second-step reaction to the structure shown in FIG. 5. Namely, it is possible to employ various structures. For example, it is possible to produce the carbonate ester (5) using the reaction device shown in FIG. 6. In this case, it is necessary to supply a mixture of the carboxylate (3), the carbonate ester (4) and a catalyst to the multistage distillation column 51 through a feed pipe 18, the preheater 20, a feed pipe 19. It is also necessary to connect the feed pipe 19 to an intermediate stage of the multistage distillation column 51.

Figure 8:
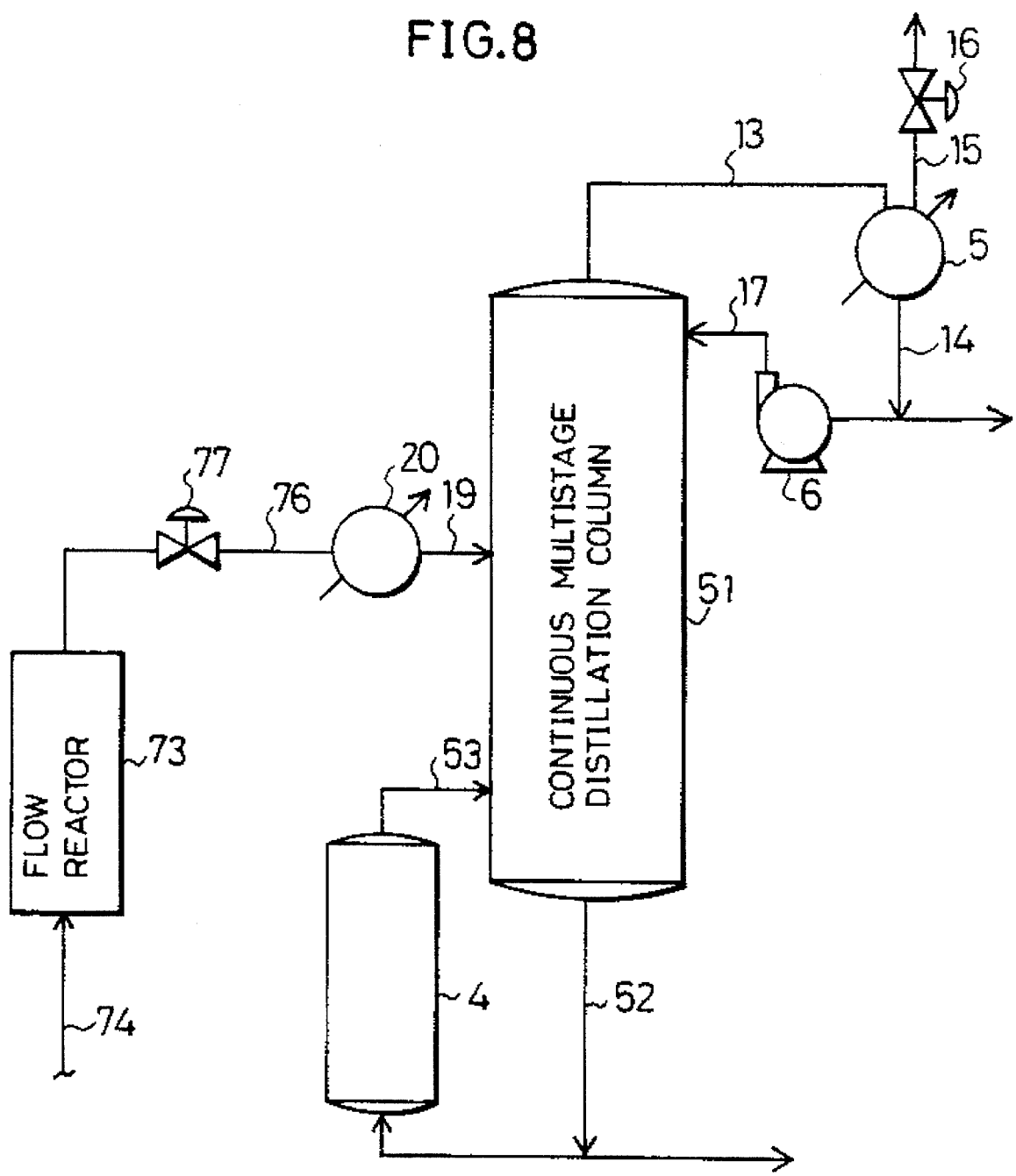

Referring now to FIG. 8, the following description explains an example of the process for preparing the carbonate ester (5) using a reaction device having a flow reactor and a multistage distillation column as reactors. For the sake of explanation, the structures performing the same functions as the structures of the above-mentioned reaction device (FIG. 6) will be designated by the same code and their description will be omitted.

As illustrated in FIG. 8, the reaction device includes the multistage distillation column 51 and a flow reactor 73 as reactors, the reboiler 4, the condenser 5, and the pump 6.

The flow reactor 73 and the multistage distillation column 51 perform a transesterification between the carboxylate (3) and the carbonate ester (4). A conduit 74 is connected to the bottom of the flow reactor 73. The conduit 74 is also connected to a feed tank (not shown) for supplying the mixture of the carboxylate (3) and the carbonate ester (4). A conduit 76 is connected to the top of the flow reactor 73 and to the preheater 20. A pressure control valve 77 is attached to the conduit 76. When there is a difference between the operating pressure of the flow reactor 73 and that of the multistage distillation column 51, the pressure control valve 77 regulates the operating pressure of the flow reactor 73.

The multistage distillation column 51 carries out vapor-liquid contacting while performing a transesterification between the carboxylate (3) and the carbonate ester (4). Other structures of the reaction device are the same as those of the above-mentioned reaction device (FIG. 6).

Next, an example of the process for preparing the carboxylate (5) using a reaction device having the above-mentioned structures is explained. For the sake of explanation, the same operations as in the above-mentioned reaction device (FIG. 6) will be briefly explained.

First, the mixture of the carboxylate (3) and the carbonate ester (4) is continuously supplied to the flow reactor 73 through the conduit 74. When the catalyst is a homogeneous catalyst, the catalyst is continuously supplied to the flow reactor 73 together with the mixture. When the catalyst is a heterogeneous catalyst, the catalyst is retained in the flow reactor 73 and the multistage distillation column 51. Moreover, when a solvent is used, it is necessary to continuously supply the solvent to the flow reactor 73 together with the mixture.

The flow reactor 73 proceeds a transesterification reaction to a degree. Thereafter, the reaction liquid in the flow reactor 73 is continuously supplied to the multistage distillation column 51 through the conduit 76.

The multistage distillation column 51 further proceeds the transesterification reaction. Namely, vapor-liquid contacting is carried out while performing the transesterification between the carboxylate (3) and carbonate ester (4) supplied to the multistage distillation column 51 in the presence of a catalyst. In other words, reaction distillation is performed.

By performing the above-mentioned reaction operations, the carbonate ester (5) is continuously produced in an efficient manner.

Figure 9:
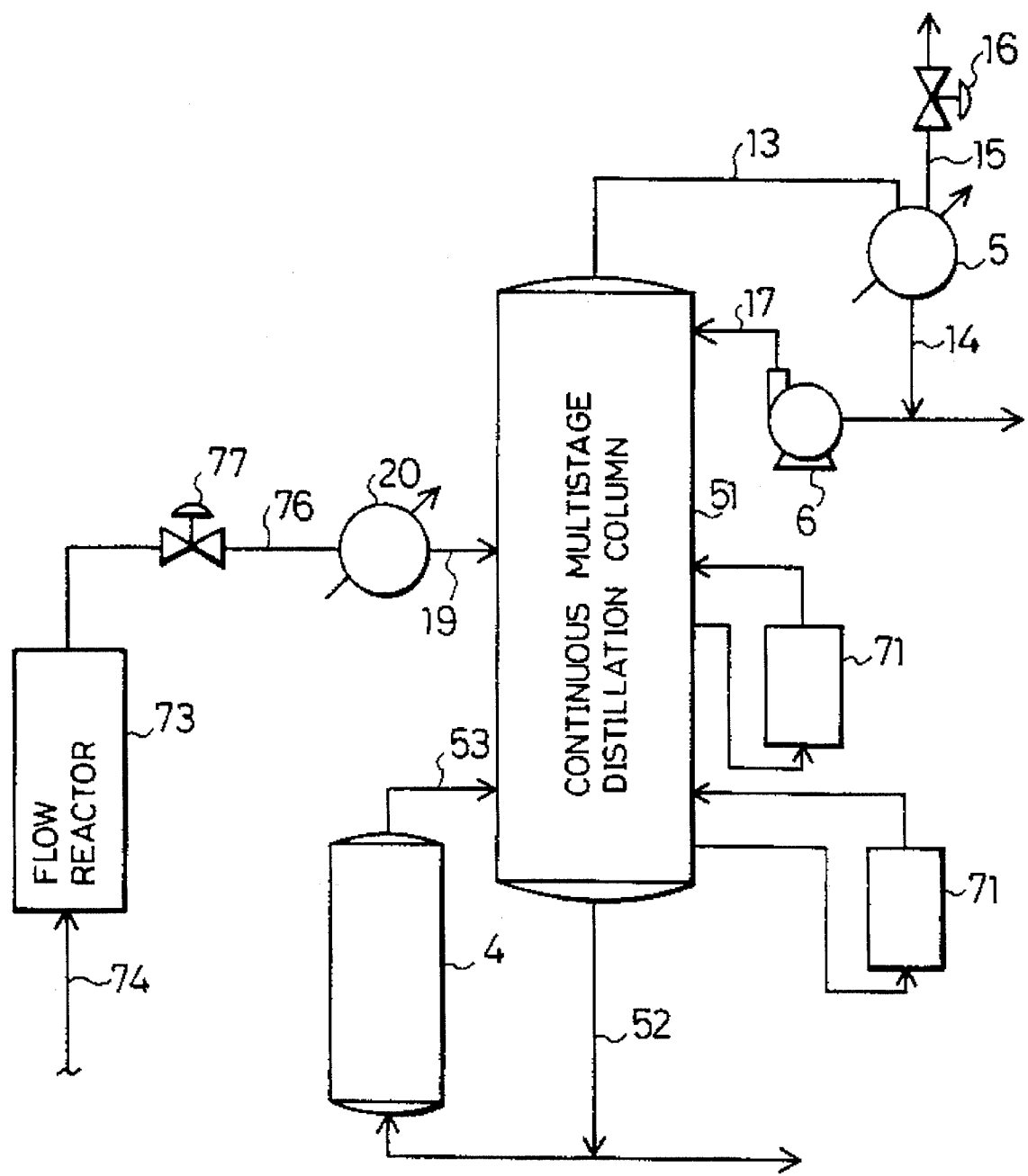

There is no need to restrict the structure of the reaction device having a multistage distillation column to the structures shown in FIGS. 6 to 8. Namely, it is possible to employ various structures. For example, when the activity of the catalyst is not sufficient or when the residence time of liquid in the multistage distillation column is relatively short, another reactor 71 may be installed in intermediate stage of the multistage distillation column 51 as illustrated in FIG. 9 (FIG. 9 shows the multistage distillation column 1 including two reactors 71 as an example). In this case, the reactor 71 removes a part of the liquid phase from the multistage distillation column 51, maintain a sufficient residence time of the liquid phase, and reflux it to the multistage distillation column 51. The number and installation position of the reactor 71 are not particularly limited.

Figure 10:
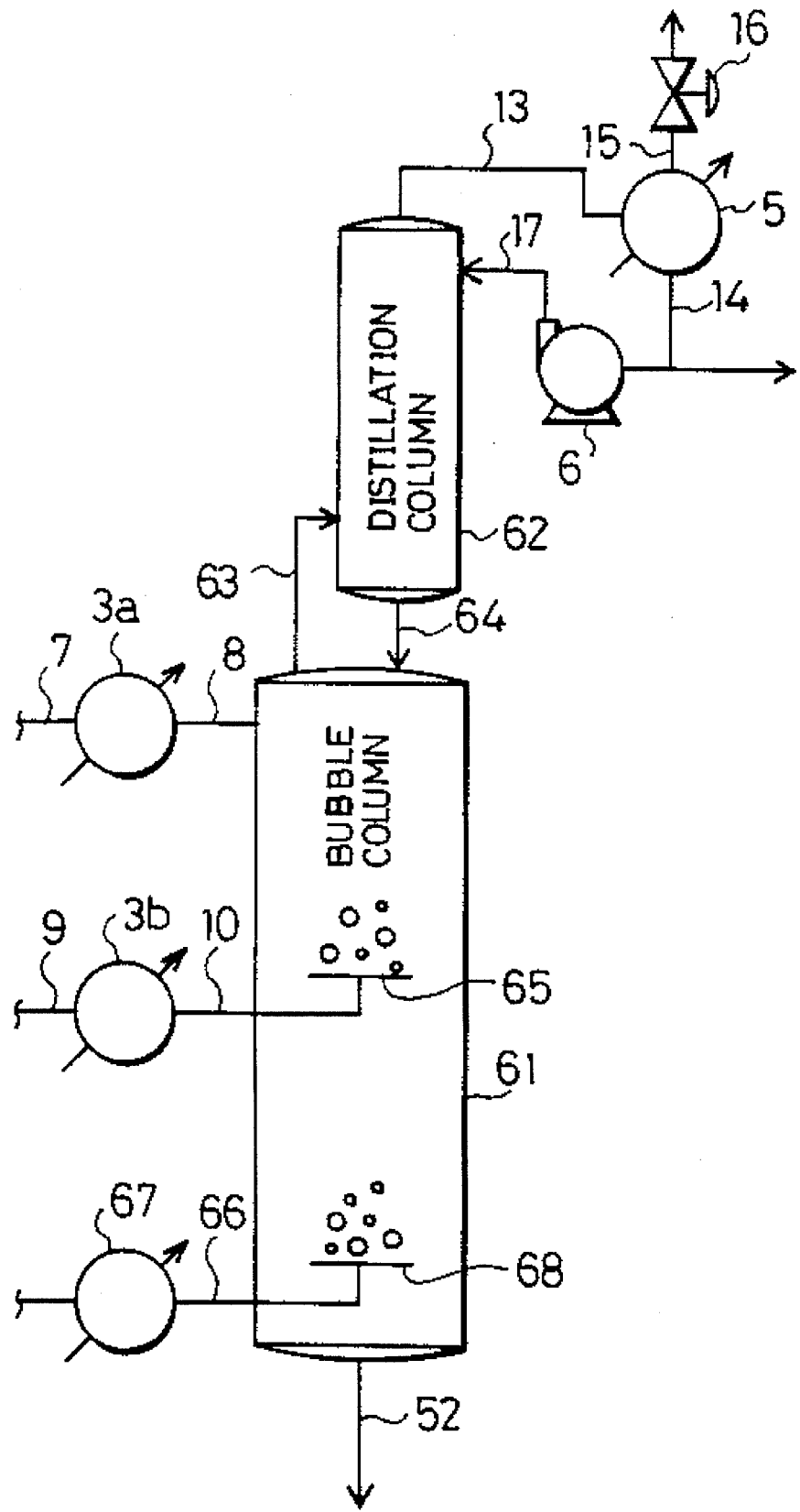

Furthermore, as illustrated in FIG. 10, the reaction device may include the bubble column 61 and the distillation column 62 as reactors instead of the multistage distillation column 51 (FIG. 6). The following description explains a reaction device including a bubble column. For the sake of explanation, the structures performing the same functions as the structures of the above-mentioned reaction device (FIG. 7) will be designated by the same code and their description will be omitted.

The bubble column 61 carries out vapor-liquid contacting while performing a transesterification between the carboxylate (3) and the carbonate ester (4). In the bubble column 61, the feed pipe 8 is connected to a portion near the top of the bubble column 61, while the feed pipe 10 is connected to an intermediate stage thereof. A conduit 66 is connected to a portion near the bottom of the bubble column 61. The conduit 66 includes a preheater 67, and introduces a gas inert to the reaction system into the bubble column 61. A redistributor 68 such as a perforated plate and a porous plate is mounted on a portion of the conduit 66 inserted into the bubble column 61. The gas facilitates the separation of the carboxylate (6) from the reaction liquid.

The distillation column 62 separates the carboxylate (6) from the reaction liquid. A reaction liquid containing a large amount of the carboxylate (6) is continuously supplied from the bubble column 61 to the distillation column 62 through the conduit 63. On the other hand, the residue is refluxed to the bubble column 61 from the distillation column 62 through the conduit 64. The preheater 3b preheats the carbonate ester (4) to a gaseous form. Other structures of the reaction device are the same as those of the above-mentioned reaction device (FIG. 7).

Next, an example of the process for preparing the carbonate ester (5) using the reaction device having the above-mentioned structures is explained below. For the sake of explanation, the same operations as in the above-mentioned reaction device (FIG. 7) will be briefly explained.

First, the carboxylate (3) is continuously supplied to the bubble column 61 through the feed pipe 8, while the carbonate ester (4) is continuously supplied to the bubble column 61 through the feed pipe 10. An inert gas is continuously supplied to the bubble column 61 through the conduit 66. When the catalyst is a homogeneous catalyst, the catalyst is continuously supplied to the bubble column 61 together with the carboxylate (3). When the catalyst is a heterogeneous catalyst, the catalyst is retained in the bubble column 61. Moreover, when a solvent is used, it is necessary to continuously supply the solvent to the bubble column 61 together with the carboxylate (3) or the carbonate ester (4).

Vapor-liquid contacting is carried out while performing a transesterification between the carboxylate (3) and carbonate ester (4) supplied to the bubble column 61 in the presence of a catalyst. Namely, reaction distillation is performed. Then, the column bottom liquid containing the produced carbonate ester (5) is continuously removed from the bubble column 61. In short, the carbonate ester (5) as the object is continuously removed as the residue from the reaction system.

On the other hand, a reaction liquid containing a large amount of the carboxylate (6) is continuously supplied to the distillation column 62. The reaction liquid supplied to the distillation column 62 is continuously distilled, and the residue is refluxed to the bubble column 61. Meanwhile, a gas containing the by-produced carboxylate (6) is continuously condensed to a distillate by the condenser 5. Namely, the by-produced carboxylate (6) is continuously removed as the distillate from the reaction system.

By carrying out the above-mentioned reaction, the carbonate ester (5) is continuously produced in an efficient manner. Additionally, if the separation of the carboxylate (6) from the reaction liquid is easily performed, it is possible to omit the conduit 66 for feeding a gas.

There is no need to restrict the structure of the reaction device used in the process for preparing carbonate esters of the present invention to the structures shown in FIGS. 1 to 10. Namely, it is possible to employ various structures.

As described above, the process for preparing carbonate esters according to the present invention produces the carboxylate (3) by performing a transesterification between the carboxylate (1) and the aromatic hydroxy compound represented by formula (2) in the presence of a catalyst, and then produces the carbonate ester (5) by performing a transesterification between the carboxylate (3) and the carbonate ester (4) in the presence of a catalyst.

This process achieves improved equilibrium conversion, and the efficient production of carbonate ester (5).

The present invention will be described in more detail by presenting the following examples and comparative examples, which should not be considered as limiting, in any way, the scope of the invention.

[EXAMPLE 1]

Carbonate ester (5) was produced using a reaction device shown in FIG. 1. A stainless reactor having a content volume of 1 L and a pressure reducing device was used as the batch reactor 1. A stainless distillation column with a height of 500 mm and an inner diameter of 20 mm, packed with a 1.5 mm$\phi$ stainless Dixon packing as a packing material, was used as the distillation column 2.

300 g methyl valerate (carboxylate (1)), 100 g phenol (an aromatic hydroxy compound), and 0.1 g dibutyltin oxide ($Bu_2SnO$) as a catalyst were supplied to the batch reactor 1 through the feed pipe 10.

The reaction liquid was stirred and heated to 240° C., and a first-step reaction was carried out at 240° C. At this time, a low boiling point component containing methanol (alcohol) as a by-product was distilled off by the distillation column 2 with a reflux ratio of 2. The temperature of the batch reactor 1 was maintained at 240° C. by operating the pressure control valve 16.

After continuing the first-step reaction for 3 hours, most of the unreacted methyl valerate and phenol were distilled off. The total amount of the distilled methanol, methyl valerate and phenol was 302 g.

Subsequently, 100 g dimethyl carbonate (carbonate ester (4)) was supplied to the batch reactor 1 through the feed pipe 10. Next, after closing the batch reactor 1, the reaction liquid was stirred at 200° C. for 30 minute, and a second-step reaction was performed until a substantially equilibrium state was achieved. Then, the pressure in the batch reactor 1 was reduced, and the unreacted dimethyl carbonate was distilled off. Next, the reaction liquid was stirred at 200° C. for 1 hour, and the first-step reaction was further continued. At this time, a low boiling point component containing methyl valerate (carboxylate (6)) as a by-product was distilled off by the distillation column 2 with a reflux ratio of 2.

After the completion of the second-step reaction, the unreacted phenyl valerate (carboxylate (3)) was distilled off. As a result, a 53.7 g reaction mixture containing 95.5 weight percent of diphenyl carbonate (carboxylate (5)) was obtained. The yield of the diphenyl carbonate was 45.1 mole percent based on the substantially consumed phenol.

As is clear from the results, it is possible to efficiently produce the carbonate ester (5) by carrying out the process of this example.

[EXAMPLE 2]

Carbonate ester (5) was continuously produced using a reaction device shown in FIG. 3. A stainless distillation column with a height of 2.5 m and an inner diameter of 20 mm, packed with a 1.5 mm$\phi$ stainless Dixon packing as a packing material, was used as the multistage distillation column 31. The feed pipe 8 was connected to a portion 1 m below the top of the multistage distillation column 31, while the feed pipe 10 was connected to a portion 500 mm above the bottom of the multistage distillation column 31. Here, heat necessary for distillation was supplied by heating the bottom of the multistage distillation column 31 with a heater instead of heating the column bottom liquid using the reboiler 4.

A stainless flow reactor with a length of 200 mm and an inner diameter of 20 mm was used as the reactor 33. A stainless distillation column with a height of 1.5 m and an inner diameter of 20 mm, packed with a 1.5 mm$\phi$ stainless Dixon packing as a packing material, was used as the multistage distillation column 32. The conduit 36 was connected to a portion 500 mm below the top of the multistage distillation column 32. Here, heat necessary for distillation was supplied by heating the bottom of the multistage distillation column 32 with a heater instead of heating the column bottom liquid using the reboiler 4. The multistage distillation column 32 includes a pressure reducing device.

A feed liquid A containing a raw material whose main component was phenol and titanium tetraphenoxide (Ti(OPh)$_4$) as a catalyst was continuously supplied to the multistage distillation column 31 through the feed pipe 8. The flow rate of the feed liquid A per hour was 24.7 g/hr.

Additionally, a feed liquid B (partly in a gaseous form) containing a raw material whose main component was methyl valerate was continuously supplied to the multistage distillation column 31 through the feed pipe 10. The flow rate of the feed liquid B per hour was 58.8 g/hr. The titanium tetraphenoxide was added so that the amount of titanium added was 500 ppm based on the raw material (the total amount of the methyl valerate and phenol).

The operating conditions of the multistage distillation column 31 were a column bottom temperature of 243° C., a column top pressure of 4 kg/cm$^2$ and a reflux ratio of 2. The reaction conditions, i.e., the flow rates and compositions of the feed liquids A and B, and the operating conditions of the multistage distillation column 31 are shown in Table 1.

Vapor-liquid contacting was carried out while performing a transesterification between the methyl valerate and phenol (first-step reaction) in the multistage distillation column 31. Then, a residue C containing the produced phenyl valerate was continuously fed to the reactor 33, while a distillate D containing the by-produced methanol was continuously removed from the reaction system. The flow rate of the residue C per hour was 75.0 g/hr, and the flow rate of the distillate D per hour was 8.5 g/hr.

Next, a feed liquid E as a raw material whose main component was dimethyl carbonate was continuously supplied through the conduit 34a to the reactor 33. Namely, the residue C and the feed liquid E were continuously supplied to the reactor 33. The flow rate of the feed liquid E per hour was 37.1 g/hr. Vapor-liquid contacting was carried out while performing a transesterification between the phenyl valerate and dimethyl carbonate (second-step reaction) in the reactor 33. In short, the second-step reaction was continued until a substantially equilibrium state was achieved. The pressure in the reactor 33 was maintained at 10 kg/cm$^2$, i.e., to be not lower than the vapor pressure of the reaction liquid by operating the pressure control valve 37, while the temperature in the reactor 33 was maintained at 200° C. Thus, the reaction liquid in the reactor 33 was maintained in a liquid phase.

Next, the reaction liquid in the reactor 33 was continuously fed to the multistage distillation column 32. The operating conditions of the multistage distillation column 32 were a column bottom temperature of 219° C., a column top pressure of 100 mmHg, and a reflux ratio of 1. The reaction conditions, i.e., the flow rate and composition of the feed liquid E, and the operating conditions of the reactor 33 and the multistage distillation column 32 are shown in Table 2.

Vapor-liquid contacting was carried out while performing a transesterification between the phenyl valerate and dimethyl carbonate (second-step reaction) in the multistage distillation column 32. Namely, the second-step reaction was further continued in the multistage distillation column 32. Then, a residue F containing the produced diphenyl carbonate was continuously removed from the reaction system. In addition, a distillate G containing the by-produced methyl valerate and the unreacted dimethyl carbonate and phenol was continuously removed from the reaction system. The flow rate of the residue F per hour was 28.1 g/hr, and the flow rate of the distillate G per hour was 84.0 g/hr.

Thereafter, the composition of the residue F was analyzed. When the raw materials (the total amount of the methyl valerate, phenol and dimethyl carbonate) were supplied at a flow rate of 1 kg/hr, the yield of the diphenyl carbonate was 231 g/kg·hr. The yield of the diphenyl carbonate was 99 mole percent based on the substantially consumed phenol. Table 3 shows the results of the reaction, i.e., the flow rates and compositions of the distillates D and G and the residues C and F, and the yield of the diphenyl carbonate.

The distillate G was separated into the unreacted dimethyl carbonate and other component containing methyl valerate by distillation. The collected dimethyl carbonate was again supplied to the reactor 33 through the conduit 34a. The collected other component containing the methyl valerate was again supplied to the multistage distillation column 31 through the feed pipe 10. Namely, the methyl valerate was not substantially consumed. Furthermore, the residue F was separated into the diphenyl carbonate and titanium tetraphenoxide by distillation. The collected titanium tetraphenoxide was again supplied to the multistage distillation column 31 through the feed pipe 8.

[EXAMPLE 3]

Diphenyl carbonate was continuously produced using a reaction device similar to that of Example 2 except that methyl butyrate (carboxylate (1)) and lead diphenoxide (Pb(OPh)$_2$) as a catalyst were used in place of methyl valerate and titanium tetraphenoxide of Example 2, respectively. The lead diphenoxide was added so that the amount of lead added was 1000 ppm based on the raw material (the total amount of the methyl butyrate and phenol).

The reaction conditions, i.e., the flow rates and compositions of the feed liquids A and B, and the operating conditions of the multistage distillation column 31 are shown in Table 1. Additionally, the reaction conditions, i.e., the flow rate and composition of the feed liquid E, and the operating conditions of the reactor 33 and the multistage distillation column 32 are shown in Table 2.

Thereafter, the composition of the residue F was analyzed. The yield of the diphenyl carbonate was 244 g/kg·hr or 99 mole percent. Table 3 shows the results of the reaction, i.e., the flow rates and compositions of the distillates D and G and the residues C and F, and the yield of the diphenyl carbonate.

[EXAMPLE 4]

Diphenyl carbonate was continuously produced using a reaction device similar to that of Example 2 except that methyl hexanoate (carboxylate (1)) was used in place of methyl valerate of Example 2.

The reaction conditions, i.e., the flow rates and compositions of the feed liquids A and B, and the operating conditions of the multistage distillation column 31 are shown in Table 1. Additionally, the reaction conditions, i.e., the flow rate and composition of the feed liquid E, and the operating conditions of the reactor 33 and the multistage distillation column 32 are shown in Table 2.

Thereafter, the composition of the residue F was analyzed. The yield of the diphenyl carbonate was 189 g/kg·hr or 91 mole percent. Table 3 shows the results of the reaction, i.e., the flow rates and compositions of the distillates D and G and the residues C and F, and the yield of the diphenyl carbonate.

TABLE 1

| | Feed liquid A | | | Feed liquid B | | | Multistage distillation column 31 | | |
| --- | --- | --- | --- | --- | --- | --- | --- | --- | --- |
| | | composition | | | composition | | tempe-rature at the | pres-sure at the | |
| Example | flow rate (g/hr) | aromatic hydroxyl compound (weight %) | catalyst (ppm) | flow rate (g/hr) | carboxylate (1) (weight %) | aromatic hydroxyl compound (weight %) | bottom of column (°C.) | top of column (kg/cm$^2$) | reflux ratio |
| 2 | 24.7 | phenol 100 | Ti(OPh)$_4$ 500 | 58.8 | methyl valerate 69.2 | phenol 30.8 | 243 | 4 | 2 |
| 3 | 22.6 | phenol 100 | Pb(OPh)$_2$ 1000 | 47.1 | methyl butyrate 84.0 | phenol 16.0 | 249 | 4.5 | 2 |
| 4 | 21.1 | phenol 100 | Ti(OPh)$_4$ 500 | 63.7 | methyl hexanoate 84.0 | phenol 14.2 | 249 | 3.5 | 1 |

TABLE 2

| | Feed liquid E | | | Reactor 33 | | Multistage distillation column 32 | | |
| --- | --- | --- | --- | --- | --- | --- | --- | --- |
| | flow | composition | | reaction tempe- | reaction | tempera-ture at the bottom of | pres-sure at the top of | |
| Example | rate (g/hr) | carbonate ester (4) (weight %) | carboxylate (1) (weight %) | rature (°C.) | pressure kg/cm$_2$) | column (°C.) | column (mmHg) | reflux ratio |
| 2 | 37.1 | dimethyl carbonate 95.7 | methyl valerate 4.3 | 200 | 10 | 210 | 100 | 1 |
| 3 | 34.3 | dimethyl carbonate 94.2 | methyl butyrate 5.8 | 200 | 10 | 240 | 140 | 1 |
| 4 | 40.8 | dimethyl carbonate 98.8 | methyl hexanoate 1.2 | 200 | 10 | 240 | 150 | 1 |

TABLE 3

| Example | Distillate D flow rate (g/hr) | Distillate D composition (wt %) | Residue C flow rate (g/hr) | Residue C composition (wt %) | Distillate G flow rate (g/hr) | Distillate G composition (wt %) | Residue F flow rate (g/hr) | Residue F composition (wt %) | Reaction result yield (g/kg·hr) | Reaction result yield (mole %) |
|---|---|---|---|---|---|---|---|---|---|---|
| 2 | 8.5 | methanol 99.9 | 75.0 | phenyl valerate 62.3 phenol 24.1 methyl valerate 13.5 | 84.0 | dimethyl carbonate 28.1 phenol 21.6 methyl valerate 50.3 | 28.1 | diphenyl carbonate 99 | 231 | 99 |
| 3 | 7.7 | methanol 99.9 | 62.2 | phenyl butyrate 63.3 phenol 12.1 methyl butyrate 24.6 | 70.7 | dimethyl carbonate 30.6 phenol 10.6 methyl butyrate 58.8 | 25.8 | diphenyl carbonate 99 | 244 | 99 |
| 4 | 7.2 | methanol 99.9 | 77.9 | phenyl hexanoate 55.2 phenol 11.6 methyl hexanoate 33.2 | 94.5 | dimethyl carbonate 32.0 phenol 9.6 methyl hexanoate 58.4 | 23.7 | diphenyl carbonate 84.7 | 189 | 91 |

As is clear from the results of Examples 2 to 4, it is possible to continuously produce the carbonate ester (5) in an efficient manner by carrying out the processes of these examples.

[EXAMPLE 5]

Carboxylate (3) was continuously produced by carrying out a first-step reaction using a reaction device shown in FIG. 5. However, the multistage distillation column 31 of Example 2 was used as a multistage distillation column 51. The operating conditions of the multistage distillation column 51 were the same as those of the multistage distillation column 31 of Example 2. The reaction conditions, i.e., the flow rates and compositions of the feed liquids A and B, and the operating conditions of the multistage distillation column 51 are shown in Table 4. Additionally, the flow rates of the distillate D and the residue C, and the composition of the residue C are shown in Table 5.

Thereafter, the composition of the residue C was analyzed. When the raw materials (the total amount of the methyl valerate and phenol) were supplied at a flow rate of 1 kg/hr, the yield of the phenyl valerate (carboxylate (3)) was 561 g/kg·hr. The conversion of the methyl valerate was 74.8 mole percent, and the conversion of the phenol was 57.8 mole percent. Table 5 shows the results of the reaction, i.e., the yield of the phenyl valerate and the conversion of the methyl valerate and phenol.

[EXAMPLE 6]

Phenyl valerate was continuously produced using a reaction device similar to that of Example 5 except that a stainless plate column having a height (the distance between a stage to which the feed pipe 10 was connected are a stage to which the feed pipe 8 was connected) of 1.5 m and 30 plates was used in place of the multistage distillation column 51 of Example 5. The reaction conditions, i.e., the flow rates and compositions of the feed liquids A and B, and the operating conditions of the plate column are shown in Table 4.

Thereafter, the composition of the residue C was analyzed. The yield of the phenyl valerate was 493 g/kg·hr. The conversion of the methyl valerate was 48.0 mole percent, and the conversion of the phenol was 79.0 mole percent. Table 5 shows the results of the reaction, i.e., the flow rates of the distillate D and the residue C, the composition of the residue C, the yield of the phenyl valerate, and the conversion of the methyl valerate and phenol.

[EXAMPLE 7]

Phenyl hexanoate (carboxylate (3)) was continuously produced using a reaction device similar to that of Example 6 except that methyl hexanoate (carboxylate (1)) and dibutyltin oxide as a catalyst were used in place of methyl valerate and titanium tetraphenoxide of Example 6, respectively. The reaction conditions, i.e., the flow rates and compositions of the feed liquids A and B, and the operating conditions of the plate column are shown in Table 4. The dibutyltin oxide was added so that the amount of tin added was 500 ppm based on the raw material (the total amount of the methyl hexanoate and phenol).

Thereafter, the composition of the residue C was analyzed. The yield of the phenyl hexanoate was 696 g/kg·hr. The conversion of the methyl hexanoate was 78.7 mole percent, and the conversion of the phenol was 85.1 mole percent. Table 5 shows the results of the reaction, i.e., the flow rates of the distillate D and the residue C, the composition of the residue C, the yield of the phenyl hexanoate, and the conversion of the methyl hexanoate and phenol.

[EXAMPLE 8]

Phenyl valerate was continuously produced using a reaction device similar to that of Example 6 except that a feed liquid B (partly in a gaseous form) containing a raw material whose main component was methyl valerate, and cyclohexane (a solvent) forming an azeotrope with the by-produced methanol was continuously supplied to the plate column through the feed pipe 10. The reaction conditions, i.e., the flow rates and compositions of the feed liquids A and B, and the operating conditions of the plate column are shown in Table 4.

Thereafter, the composition of the residue C was analyzed. The yield of the phenyl valerate was 658 g/kg·hr. The conversion of the methyl valerate was 73.8 mole percent, and the conversion of the phenol was 83.0 mole percent. Table 5 shows the results of the reaction, i.e., the flow rates of the distillate D and the residue C, the composition of the residue C, the yield of the phenyl valerate, and the conversion of the methyl valerate and phenol.

[EXAMPLE 9]

Phenyl valerate was continuously produced using a reaction device similar to that of Example 6 except that a feed liquid B (partly in a gaseous form) as a raw material whose main component was methyl valerate and nitrogen gas as an inert gas was continuously supplied to the plate column through the feed pipe 10. The reaction conditions, i.e., the flow rates and compositions of the feed liquids A and B, and the operating conditions of the plate column are shown in Table 4.

Thereafter, the composition of the residue C was analyzed. The yield of the phenyl valerate was 659 g/kg·hr. The conversion of the methyl valerate was 75.6 mole percent, and the conversion of the phenol was 80.0 mole percent. Table 5 shows the results of the reaction, i.e., the flow rates of the distillate D and the residue C, the composition of the residue C, the yield of the phenyl valerate, and the conversion of the methyl valerate and phenol.

[EXAMPLE 10]

Titanium silicate (a catalyst, the atom ratio Si/Ti=42) with an MFI structure was compression-molded, and then granulated into a 20-mesh to 40-mesh material. The resulting titanium silicate was mixed with a 1.5 mmφ stainless Dixon packing (packing material) at a volume ratio of 1:1, and employed as a packing material instead of the Dixon packing used in Example 5. Then, phenyl valerate was continuously produced using a reaction device similar to that of Example 5 except that a feed liquid A as a raw material whose main component was phenol was continuously supplied to the multistage distillation column 51 through the feed pipe 8. The reaction conditions, i.e., the flow rates and compositions of the feed liquids A and B, and the operating conditions of the multistage distillation column 51 are shown in Table 4.

Thereafter, the composition of the residue C was analyzed. The yield of the phenyl valerate was 668 g/kg·hr. The conversion of the methyl valerate was 92.8 mole percent, and the conversion of the phenol was 66.5 mole percent. Table 5 shows the results of the reaction, i.e., the flow rates of the distillate D and the residue C, the composition of the residue C, the yield of the phenyl valerate, and the conversion of the methyl valerate and phenol.

[EXAMPLE 11]

Carboxylate (3) was continuously produced by carrying out a first-step reaction using a reaction device shown in FIG. 7. A stainless bubble column with a height of 2 mm and an inner diameter of 20 mm, packed with a 8 mmφ porcelain Raschig ring, was used as the bubble column 61. The feed pipe 8 was connected to near the top of the bubble column 6, and the feed pipe 10 was connected to a portion 100 mm above the column bottom. A perforated plate was used as the redistributor 65. In addition, a stainless distillation column with a height of 500 mm, packed with a 1.5 mmφ stainless Dixon packing as a packing material, was used as the distillation column 62. The feed liquid B was continuously supplied in a gaseous form.

Other structures of the reaction device were the same as those of the reaction device used in Example 5. Phenyl valerate was continuously produced. The reaction conditions, i.e., the flow rates and compositions of the feed liquids A and B, and the operating conditions of the distillation column 62 are shown in Table 4.

Thereafter, the composition of the residue C was analyzed. The yield of the phenyl valerate was 323 g/kg·hr. The conversion of the methyl valerate was 29.1 mole percent, and the conversion of the phenol was 62.0 mole percent. Table 5 shows the results of the reaction, i.e., the flow rates of the distillate D and the residue C, the composition of the residue C, the yield of the phenyl valerate, and the conversion of the methyl valerate and phenol.

TABLE 4

| | Feed liquid A | | | Feed liquid B | | | temperature | pressure | |
|---|---|---|---|---|---|---|---|---|---|
| | | composition | | | composition | | at the | at the | |
| Example | flow rate (g/hr) | aromatic hydroxyl compound (weight %) | catalyst (ppm) | flow rate (g/hr) | carboxylate (1) (weight %) | aromatic hydroxyl compound (weight %) | bottom of column (°C.) | top of column (kg/cm$^2$) | reflux ratio |
| 5 | 24.7 | phenol 100 | Ti(OPh)$_4$ 500 | 58.8 | methyl valerate 69.2 | phenol 30.8 | 243 | 4 | 2 |
| 6 | 30.1 | phenol 100 | Ti(OPh)$_4$ 500 | 61.2 | methyl valerate 100 | — | 248 | 4 | 0.5 |
| 7 | 40.2 | phenol 100 | Bu$_2$SnO 500 | 60.1 | methyl hexanoate 100 | — | 250 | 3 | 2 |
| 8 | 30.3 | phenol 100 | Ti(OPh)$_4$ 500 | 60.1 | methyl valerate 70 cyclohexane 30 | — | 250 | 3 | 0.5 |
| 9 | 29.5 | phenol | Ti(OPh)$_4$ | 39.8 | methyl valerate | — | 250 | 3 | 2 |

TABLE 4-continued

| | Feed liquid A | | | Feed liquid B | | | tempe- rature at the bottom of column (°C.) | pres- sure at the top of column (kg/ cm²) | reflux ratio |
|---|---|---|---|---|---|---|---|---|---|
| Exam- ple | flow rate (g/hr) | composition aromatic hydroxyl compound (weight %) | catalyst (ppm) | flow rate (g/hr) | composition carboxylate (1) (weight %) | aromatic hydroxyl compound (weight %) | | | |
| 10 | 25.1 | 100 phenol 100 | 500 — | 22.2 | 100 gaseous nitrogen 60 ml/min methyl valerate 100 | — | 280 | 4 | 3 |
| 11 | 30.3 | phenol 100 | Ti(OPh)₄ 500 | 79.8 | methyl valerate 100 | — | 248 | 4 | — |

TABLE 5

| | Distil- late D | Residue C | | | Results of Reaction | | |
|---|---|---|---|---|---|---|---|
| Exam- ple | flow rate (g/hr) | flow rate (g/hr) | composition (weight %) | | yield of carbox- ylate (3) (g/kg · hr) | conver- sion of carbox- late (1) (mole %) | conver- sion of aromatic hydroxyl compound (mole %) |
| 5 | 8.5 | 75.0 | phenyl valerate 62.3 | methyl valerate 13.6 phenol 24.1 | 561 | 74.8 | 57.8 |
| 6 | 18.1 | 73.2 | phenyl valerate 61.5 | methyl valerate 29.8 phenol 8.6 | 493 | 48.8 | 79.0 |
| 7 | 11.7 | 88.6 | phenyl hexanoate 78.9 | methyl hexanoate 14.3 phenol 6.8 | 696 | 78.7 | 85.1 |
| 8 | 26.7 | 63.7 | phenyl valerate 74.7 | methyl valerate 17.2 phenol 8.1 | 658 | 73.8 | 83.0 |
| 9 | 9.3 | 60.8 | phenyl valerate 76.0 | methyl valerate 14.3 phenol 9.7 | 659 | 75.6 | 80.0 |
| 10 | 5.7 | 41.6 | phenyl valerate 76.0 | methyl valerate 3.8 phenol 20.2 | 668 | 92.8 | 66.5 |
| 11 | 47.6 | 62.5 | phenyl valerate 56.9 | methyl valerate 24.7 phenol 18.4 | 323 | 29.1 | 62.0 |

[COMPARATIVE EXAMPLE]

29.1 g methyl valerate, 23.5 g phenol and 0.1 g titanium tetraphenoxide were introduced into a stainless autoclave having a content volume of 100 ml, a temperature meter, a pressure meter and a magnetic stirring device. A vapor phase portion was substituted by nitrogen gas. Thereafter, the temperature inside the autoclave was raised to 200° C. over 30 minutes by heating the reaction liquid with an external heater while stirring the reaction liquid. Then, a reaction was performed for 3 hours while maintaining the temperature at 200° C. At this time, the pressure in the autoclave was increased to 4.5 kg/cm².

Next, the autoclave was cooled and the reaction liquid was removed. Then, the composition of the reaction liquid was analyzed. The reaction liquid only contained 1.12 g phenyl valerate, and the yield was lowered to 21.3 g with respect to 1 kilogram of the raw materials (the total amount of the methyl valerate and phenol).

As is clear from the results of Examples 5 to 11 and Comparative Example 1, the reaction efficiency (equilibrium conversion) of the first-step reaction was improved by performing the processes of these examples. It is therefore possible to continuously produce the carboxylate (3) in an efficient manner.

[EXAMPLE 12]

Carbonate ester (5) was continuously produced by carrying out a second-step reaction using a reaction device shown in FIG. 5. A stainless distillation column with a height of 2.5 m and an inner diameter of 20 mm, packed with a 1.5 mmϕ stainless Dixon packing as a packing material, was used as the multistage distillation column 51. The feed pipe 8 was connected to a portion 500 mm below the top of the multistage distillation column 51, while the feed pipe 10 was connected to a portion 750 mm above the bottom of the multistage distillation column 51. Here, heat necessary for distillation was supplied by heating the bottom of the multistage distillation column 51 instead of heating the column bottom liquid using the reboiler 4.

A feed liquid H containing a raw material whose main component was phenyl acetate (carboxylate (3)) and titanium tetraphenoxide as a catalyst was continuously supplied to the multistage distillation column 51 through the feed pipe 8. The flow rate of the feed liquid H per hour was 50 g/hr.

Additionally, a feed liquid J (partly in a gaseous form) as a raw material whose main component was diethyl carbonate (carbonate ester (4)) was continuously supplied to the multistage distillation column 51 through the feed pipe 10.

The flow rate of the feed liquid J per hour was 50 g/hr. The titanium tetraphenoxide was added so that the amount of titanium added was 500 ppm based on the raw material (the total amount of the phenyl acetate and diethyl carbonate).

The operating conditions of the multistage distillation column 51 were a column bottom temperature of 200° C., a column top pressure of 100 mmHg, and a reflux ratio of 2. Table 6 shows the reaction conditions, i.e., the flow rates and compositions of the feed liquids H and J, and the operating conditions of the multistage distillation column 51.

Vapor-liquid contacting was carried out while performing a transesterification between the phenyl acetate and the diethyl carbonate in the multistage distillation column 51. Then, the residue F containing the produced diphenyl carbonate (carbonate ester (5)), and the distillate G containing the by-produced ethyl acetate (carboxylate (6)) and the unreacted diethyl carbonate were continuously removed from the reaction system. The flow rate of the residue F per hour was 36.0 g/hr, and the flow rate of the distillate G per hour was 64.0 g/hr.

Thereafter, the composition of the residue F was analyzed. When the raw materials (the total amount of the phenyl acetate and diethyl carbonate) were supplied at a flow rate of 1 kg/hr, the yield of the diphenyl carbonate was 322 g/kg·hr. The conversion of the phenyl acetate was 91.6 mole percent. Table 8 shows the results of the reaction, i.e., the flow rates of the distillate G and residue F, the composition of the residue F, the yield of the diphenyl carbonate, and the conversion of phenyl acetate.

[EXAMPLE 13]

Diphenyl carbonate was continuously produced using a reaction device similar to that of Example 12 except that phenyl propionate (carboxylate (3)), dipropyl carbonate (carbonate ester (4)) and dibutyltin oxide as a catalyst were used in place of phenyl acetate, diethyl carbonate and titanium tetraphenoxide of Example 12, respectively. The reaction conditions, i.e., the flow rates and compositions of the feed liquids H and J, and the operating conditions of the multistage distillation column 51 are shown in Table 6. The dibutyltin oxide was added so that the amount of tin added was 500 ppm based on the raw material (the total amount of the phenyl propionate and dipropyl carbonate).

Thereafter, the composition of the residue F was analyzed. The yield of the diphenyl carbonate was 352 g/kg·hr. The conversion of the phenyl propionate was 98.9 mole percent. Table 8 shows the results of the reaction, i.e., the flow rates of the distillate G and the residue F, the composition of the residue F, the yield of the diphenyl carbonate, and the conversion of the phenyl propionate.

[EXAMPLE 14]

Carbonate ester (5) was continuously produced using a reaction device shown in FIG. 8. A stainless distillation column with a height of 1.5 m and an inner diameter of 20 mm, packed with a 1.5 mmφ stainless Dixon packing as a packing material, was used as the multistage distillation column 51. The feed pipe 19 was connected to a portion 500 mm below the top of the distillation column 51. Here, heat necessary for distillation was supplied by heating the bottom of the multistage distillation column 51 with a heater instead of heating the column bottom liquid using the reboiler 4.

A stainless flow reactor with a length of 100 mm and an inner diameter of 20 mm was used as the flow reactor 73. A feed liquid K containing a raw material whose main components were phenyl acetate (carboxylate (3)) and dimethyl carbonate (carbonate ester (4)), and a dibutyltin oxide as a catalyst were continuously supplied to the flow reactor 73 through the conduit 74. The flow rate of the feed liquid K per hour was 120 g/hr. The dibutyltin oxide was added so that the amount of tin added was 500 ppm based on the raw material (the total amount of the phenyl acetate and dimethyl carbonate).

Regarding the operating conditions of the flow reactor 73, the reaction temperature was 200° C. After performing a transesterification reaction to a degree in the flow reactor 73, the reaction liquid (partly in a gaseous form) was continuously supplied to the multistage distillation column 51. The flow rate of the feed liquid K per hour was 120 g/hr. The pressure in the flow reactor 73 was controlled to be 10 kg/cm$^2$, i.e., not lower than the vapor pressure of the reaction liquid by operating the pressure control valve 77. Therefore, the reaction liquid in the flow reactor 73 was maintained in a liquid phase.

The operating conditions of the multistage distillation column 51 were a column bottom temperature of 220° C., a column top pressure of 100 mmHg, and a reflux ratio of 1. Table 7 shows the reaction conditions, i.e., the flow rates and compositions of the feed liquid K, and the operating conditions of reactor 73 and the multistage distillation column 51.

Vapor-liquid contacting was carried out while performing a transesterification between the phenyl acetate and the dimethyl carbonate in the multistage distillation column 51. Then, the residue F containing the produced diphenyl carbonate and the distillate G containing the by-produced methyl acetate (carboxylate (6)) and the unreacted dimethyl carbonate were continuously removed from the reaction system. The flow rate of the residue F per hour was 47.2 g/hr, and the flow rate of the distillate G per hour was 72.8 g/hr.

Thereafter, the composition of the residue F was analyzed. The yield of the diphenyl carbonate was 390 g/kg·hr. The conversion of the diphenyl acetate was 99.2 mole percent. Table 8 shows the results of the reaction, i.e., the flow rates of the distillate G and the residue F, the composition of the residue F, the yield of the diphenyl carbonate, and the conversion of the phenyl acetate.

[EXAMPLE 15]

Diphenyl carbonate was continuously produced using a reaction device similar to that of Example 14 except that phenyl valerate (carboxylate (3)) and titanium tetraphenoxide as a catalyst were used in place of the phenyl acetate and dibutyltin oxide of Example 14, respectively. However, the phenyl valerate used as the raw material contained methyl valerate and phenol that were the unreacted compounds in the reaction of synthesizing the phenyl valerate. Table 7 shows the reaction conditions, i.e., the flow rate and composition of the feed liquid K, and the operating conditions of the flow reactor 73 and the multistage distillation column 51. The titanium tetraphenoxide was added so that the amount of titanium added was 700 ppm based on the raw material (the total amount of the phenyl valerate and dimethyl carbonate).

Thereafter, the composition of the residue F was analyzed. The yield of the diphenyl carbonate was 243 g/kg·hr. The conversion of the phenyl valerate was 99.0 mole percent. Table 8 shows the results of the reaction, i.e., the flow rates of the distillate G and residue F, the composition of the residue F, the yield of the diphenyl carbonate, and the conversion of the phenyl valerate.

[EXAMPLE 16]

Carbonate ester (5) was continuously produced by carrying out a second-step reaction using a reaction device shown in FIG. 10. A stainless bubble column with a height of 2 m and an inner diameter of 20 mm, packed with an 8 mmφ porcelain Raschig ring, was used as the bubble column 61. The feed pipe 8 was connected to near the top of the bubble column 61, and the feed pipe 10 was connected to a portion 1 m above the column bottom. Perforated plates were used as the redistributors 65 and 68. In addition, a stainless distillation column with a height of 500 mm, packed with a 1.5 mmφ stainless Dixon packing as a packing material, was used as the distillation column 62.

A feed liquid H containing a raw material whose main component was phenyl acetate and lead diphenoxide as a catalyst was continuously supplied to the bubble column 61 through the feed pipe 8. The flow rate of the feed liquid H per hour was 60.1 g/hr. A feed liquid J as a raw material whose main component was dimethyl carbonate was continuously supplied in a gaseous form to the bubble column 61 through the feed pipe 10. The flow rate of the feed liquid J per hour was 60.2 g/hr. Moreover, nitrogen gas was continuously supplied to the bubble column 61 through the conduit 66. The flow rate of the nitrogen gas per hour was 1 L/hr. The lead phenoxide was added so that the amount of lead added was 1000 ppm based on the raw material (the total amount of the phenyl acetate and dimethyl carbonate).

Other structures of the reaction device were the same as those of the reaction device used in Example 12. Diphenyl carbonate was continuously produced using the reaction device. Table 6 shows the reaction conditions, i.e., the flow rates and compositions of the feed liquids H and J, and the operating conditions of the distillation column 62.

Thereafter, the composition of the residue F was analyzed. The yield of the diphenyl carbonate was 302 g/kg·hr. The conversion of the phenyl acetate was 85.8 mole percent. Table 8 shows the results of the reaction, i.e., the flow rates of the distillate G and the residue F, the composition of the residue F, the yield of the diphenyl carbonate, and the conversion of the phenyl acetate.

TABLE 6

| Example | Feed liquid H flow rate (g/hr) | Feed liquid H composition carboxylate (3) (weight %) | Feed liquid H composition catalyst (ppm) | Feed liquid J flow rate (g/hr) | Feed liquid J composition carbonate esters (4) (weight %) | Temperature at the bottom of column (°C.) | Pressure at the top of column (kg/cm$^2$) | reflux ratio |
|---|---|---|---|---|---|---|---|---|
| 12 | 50 | phenyl acetate 100 | Ti(OPh)$_4$ 500 | 50 | diethyl carbonate 100 | 200 | 100 | 2 |
| 13 | 50 | phenyl propionate 100 | Bu$_2$SnO 500 | 50 | dipropyl carbonate 100 | 219 | 100 | 1 |
| 16 | 60.1 | phenyl acetate 100 | Pb(OPh)$_2$ 1000 | 60.2 | dimethyl carbonate 100 | 230 | 100 | 2 |

TABLE 7

| Example | Feed liquid K flow rate (g/hr) | Feed liquid K composition carbonate ester (4) (wt %) | Feed liquid K composition carboxylate (3) (wt %) | Feed liquid K composition others (wt %) | Feed liquid K catalyst (ppm) | Flow reactor 73 reaction temperature (°C.) | Flow reactor 73 reaction pressure (kg/cm$^2$) | temperature at the bottom of column (°C.) | Pressure at the top of column (mmHg) | reflux ratio |
|---|---|---|---|---|---|---|---|---|---|---|
| 14 | 24.7 | dimethyl carbonate 50 | phenyl acetate 50 | | Bu$_2$SnO 500 | 200 | 10 | 220 | 100 | 1 |
| 15 | 22.6 | dimethyl carbonate 36.8 | phenyl valerate 40.9 | methyl valerate 5.2 phenol 17.1 | Ti(OPh)$_4$ 700 | 200 | 10 | 221 | 100 | 1 |

TABLE 8

| | | | Result of reaction | |
|---|---|---|---|---|
| Example | Distillate G flow rate (g/hr) | Residue F flow rate (g/hr) | Residue F composition (weight %) | yield of carbonate ester (5) (g/kg · hr) | conversion ratio of carboxylate (3) (mole %) |
|---|---|---|---|---|---|
| 12 | 64.0 | 36.0 | diphenyl carbonate 89.6 | 322 | 91.6 |

TABLE 8-continued

| | Distillate G | Residue F | | Result of reaction | |
| --- | --- | --- | --- | --- | --- |
| | | | | yield of | conversion ratio of |
| Example | flow rate (g/hr) | flow rate (g/hr) | composition (weight %) | carbonate ester (5) (g/kg · hr) | carboxylate (3) (mole %) |
| 13 | 64.4 | 35.6 | diphenyl carbonate 99.0 | 352 | 98.9 |
| 14 | 72.8 | 47.2 | diphenyl carbonate 99.1 | 390 | 99.2 |
| 15 | 116.8 | 40.5 | diphenyl carbonate 99.2 | 243 | 99.0 |
| 16 | 69.4 | 50.9 | diphenyl carbonate 71.5 | 302 | 85.8 |

As is clear from the results of Examples 12 to 16, the reaction efficiency (equilibrium conversion) of the second-step reaction was improved by performing the processes of these examples. It is thus possible to continuously produce the carbonate ester (5) in an efficient manner.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for preparing carbonate esters comprising the steps of:

producing a carboxylate represented by formula (3)

$$R^1COOR^3 \qquad (3),$$

wherein $R^1$ represents an alkyl group, an alicyclic hydrocarbon group or an aryl alkyl group, and $R^3$ represents an aromatic group with or without a substituent, by performing a transesterification between a raw carboxylate, as a raw material, of formula (1)

$$R^1COOR^2 \qquad (1),$$

wherein each of $R^1$ and $R^2$ independently represents an alkyl group, an alicyclic hydrocarbon group or an aryl alkyl group, and an aromatic hydroxy compound of formula (2)

$$R^3OH \qquad (2),$$

wherein $R^3$ represents an aromatic group with or without a substituent, in the presence of a catalyst; and producing a carbonate ester of formula (5)

$$R^3O-COOR^6 \qquad (5),$$

wherein $R^3$ represents an aromatic group with or without a substituent, and $R^6$ represents a substituent selected from the group consisting of $R^3$, an alkyl group, an alicyclic hydrocarbon group and an aryl alkyl group, by performing a transesterification between said produced carboxylate and a raw carbonate ester, as a raw material, of formula (4)

$$R^4O-COOR^5 \qquad (4),$$

wherein each of $R^4$ and $R^5$ independently represents an alkyl group, an alicyclic hydrocarbon group or an aryl alkyl group, in the presence of a catalyst;

wherein the step of producing said carbonate ester includes collecting a by-produced carboxylate and wherein said by-produced carboxylate is used as said raw carboxylate.

2. The process for preparing carbonate esters according to claim 1, wherein $R^6$ is $R^3$.

3. The process for preparing carbonate esters according to claim 1, wherein the step of producing said carboxylate includes performing vapor-liquid contacting between said raw carboxylate and said aromatic hydroxy compound and continuously removing a by-produced alcohol from a reaction system.

4. The process for preparing carbonate esters according to claim 1, wherein the step of producing said carbonate ester includes performing vapor-liquid contacting between said produced carboxylate and said raw carbonate ester and continuously removing a by-produced carboxylate from a reaction system.

5. The process for preparing carbonate esters according to claim 1, wherein each of $R^4$ and $R^5$ is the same as $R^2$.

6. The process for preparing carbonate esters according to claim 1, wherein the step of producing said carboxylate is carried out within a mole ratio of said raw carboxylate to said aromatic hydroxy compound ranging from 1:100 to 100:1.

7. The process for preparing carbonate esters according to claim 1, wherein the step of producing said carbonate ester is carried out within a mole ratio of said produced carboxylate to said raw carbonate ester ranging from 1:100 to 100:1.

8. The process for preparing carbonate esters according to claim 1, wherein at least one of the step of producing said carboxylate and the step of producing said carbonate ester is performed at a reaction temperature ranging from 50° C. to 350° C.

9. The process for preparing carbonate esters according to claim 1, wherein at least one of the step of producing said carboxylate and the step of producing said carbonate ester is performed in the presence of a solvent.

10. The process for preparing carbonate esters according to claim 1, wherein, when said raw carboxylate and a by-produced alcohol form an azeotrope, a solvent is included in a reaction system so that said solvent and said alcohol form an azeotrope having an azeotropic point lower than that of said azeotrope of said raw carboxylate and said by-produced alcohol.

11. The process for preparing carbonate esters according to claim 1, wherein the step of producing said carbonate ester includes performing a transesterification between a part of said produced carboxylate and a part of said raw carbonate ester beforehand, and performing vapor-liquid contacting while performing a transesterification between said produced carboxylate and said raw carbonate ester.

12. The process for preparing carbonate esters according to claim 11, wherein the step of performing a transesterification between a part of said produced carboxylate and a part of said raw carbonate ester beforehand proceeds the transesterification by at least 10 percent of equilibrium conversion.

13. The process for preparing carbonate esters according to claim 1, wherein each of $R^1$ and $R^2$ independently represents an alkyl group having 1 to 10 carbons, an alicyclic hydrocarbon group having 3 to 10 carbons or an aryl alkyl group having 7 to 10 carbons.

14. The process for preparing carbonate esters according to claim 1, wherein said raw carboxylate is a compound whose boiling point is higher than that of a by-produced alcohol.

15. The process for preparing carbonate esters according to claim 1, wherein said raw carboxylate is a compound which does not form an azeotrope with a by-produced alcohol.

16. The process for preparing carbonate esters according to claim 1, wherein said raw carboxylate is a compound whose boiling point is lower than that of said produced carboxylate.

17. The process for preparing carbonate esters according to claim 1, wherein said produced carboxylate is a compound whose boiling point is higher than that of a by-produced carboxylate.

18. The process for preparing carbonate esters according to claim 1, wherein said produced carboxylate is a compound whose boiling point is lower than that of said carbonate ester.

19. The process for preparing carbonate esters according to claim 1, wherein said raw carboxylate is a compound selected from the group consisting of methyl acetate, ethyl acetate, propyl acetate, butyl acetate, cyclohexyl acetate, benzyl acetate, 2-ethylhexyl acetate, methyl propionate, ethyl propionate, propyl propionate, butyl propionate, methyl butyrate, ethyl butyrate, propyl butyrate, methyl isobutyrate, ethyl isobutyrate, propyl isobutyrate, methyl valerate, ethyl valerate, propyl valerate, methyl isovalerate, ethyl isovalerate, propyl isovalerate, methyl hexanoate, ethyl hexanoate, propyl hexanoate, methyl heptanoate, and ethyl heptanoate.

20. The process for preparing carbonate esters according to claim 1, wherein said raw carboxylate is a compound selected from the group consisting of methyl valerate, methyl butyrate, and methyl hexanoate.

21. The process for preparing carbonate esters according to claim 1, wherein said aromatic hydroxy compound is a compound selected from the group consisting of phenol, o-cresol, m-cresol, p-cresol, o-chlorophenol, m-chlorophenol, p-chlorophenol, o-ethylphenol, m-ethylphenol, p-ethylphenol, o-isopropylphenol, m-isopropylphenol, p-isopropylphenol, o-methoxyphenol, m-methoxyphenol, p-methoxyphenol, xylenols, α-naphthol, and β-naphthol.

22. The process for preparing carbonate esters according to claim 1, wherein said aromatic hydroxy compound is phenol.

23. The process for preparing carbonate esters according to claim 1, wherein said raw carbonate ester is a compound selected from the group consisting of dimethyl carbonate, diethyl carbonate, di-n-propyl carbonate, diisopropyl carbonates, isomers of dibutyl carbonate, isomers of dipentyl carbonate, isomers of dihexyl carbonate, isomers of diheptyl carbonate, isomers of dioctyl carbonate, isomers of dinonyl carbonate, isomers of didecyl carbonate, dicyclohexyl carbonate, dibenzyl carbonate, isomers of diphenethyl carbonate, and isomers of di(m-ethylbenzyl) carbonate.

24. The process for preparing carbonate esters according to claim 1, wherein said raw carbonate ester is a compound selected from the group consisting of dimethyl carbonate, diethyl carbonate, and di-n-propyl carbonate.

25. The process for preparing carbonate esters according to claim 1, wherein said catalyst is a compound selected from the group consisting of mineral acid, sulfonic acids, solid acid, base, metal alkoxide, Lewis acid, and a compound producing Lewis acid, metal phenoxides, lead oxides, lead salts, metal acetylacetonate complex, organotin compound, titanium silicate, and metal-substituted aluminum phosphate.

26. The process for preparing carbonate esters according to claim 1, wherein at least one of the step of producing said carboxylate and the step of producing said carbonate ester are carried out in a reactor selected from the group consisting of a batch reactor, flow reactor, and a vapor-liquid contacting reactor.

27. The process for preparing carbonate esters according to claim 1, wherein the step of producing said carboxylate and the step of producing said carbonate ester are carried out in the same reactor.

28. The process for preparing carbonate esters according to claim 1, wherein at least one of the step of producing said carboxylate and the step of producing said carbonate ester are carried out in a multistage distillation column.

29. The process for preparing carbonate esters according to claim 1, wherein at least one of the step of producing said carboxylate and the step of producing said carbonate ester are carried out in a bubble column.

30. The process for preparing carbonate esters according to claim 29, wherein one of said raw carboxylate and said aromatic hydroxy compound, which has a higher boiling point, is supplied to an upper portion of said bubble column, and the other is supplied to a lower portion of said bubble column.

31. The process for preparing carbonate esters according to claim 29, wherein one of said produced carboxylate and said raw carbonate ester, which has a higher boiling point, is supplied to an upper portion of said bubble column, and the other is supplied to a lower portion of said bubble column.

* * * * *